US008628727B2

(12) United States Patent
Van Duyne et al.

(10) Patent No.: US 8,628,727 B2
(45) Date of Patent: Jan. 14, 2014

(54) COMPOSITIONS, DEVICES AND METHODS FOR SERS AND LSPR

(75) Inventors: Richard P. Van Duyne, Wilmette, IL (US); Xiaoyu Zhang, Urbana, IL (US); Jing Zhao, Evanston, IL (US); Alyson V. Whitney, Chicago, IL (US); Jeffrey W. Elam, Elmhurst, IL (US); George C. Schatz, Evanston, IL (US); Peter C. Stair, Northbrook, IL (US); Shengli Zou, Oviedo, FL (US); Matthew Young, Allen, MI (US); Olga Lyandres, Chicago, IL (US)

(73) Assignee: Northwestern University, Evanston, IL (US)

( * ) Notice: Subject to any disclaimer, the term of this patent is extended or adjusted under 35 U.S.C. 154(b) by 1796 days.

(21) Appl. No.: 11/846,352

(22) Filed: Aug. 28, 2007

(65) Prior Publication Data

US 2013/0330815 A1 Dec. 12, 2013

Related U.S. Application Data

(63) Continuation-in-part of application No. 11/401,203, filed on Apr. 10, 2006, now abandoned.

(60) Provisional application No. 60/856,601, filed on Nov. 3, 2006, provisional application No. 60/669,727, filed on Apr. 8, 2005.

(51) Int. Cl.
*G01N 21/75* (2006.01)
*G01N 31/22* (2006.01)
*G01N 33/52* (2006.01)
*G01N 33/53* (2006.01)
*C12Q 1/04* (2006.01)
*G01J 3/44* (2006.01)
*G01N 33/00* (2006.01)

(52) U.S. Cl.
USPC .............. 422/402; 435/7.1; 435/34; 356/301; 436/86

(58) Field of Classification Search
USPC ..................................... 435/7.1, 14
See application file for complete search history.

(56) References Cited

U.S. PATENT DOCUMENTS

2004/0180379 A1  9/2004 Van Duyne et al.
2005/0244977 A1* 11/2005 Drachev et al. ................. 436/86

OTHER PUBLICATIONS

Van Duyne et al. J Chem Phys. 99 (3), Aug. 1, 1993.*
Van Duyne et al. J Chem Phys. 99 (3), Aug. 1, 1993, pp. 2101-2115.*
Whitney et al., "Localized Surface Plasmon Resonance Nanosensor: A High-Resolution Distance-Dependence Study Using Atomic Layer Deposition", The Journal of Physical Chemistry B, Oct. 5, 2005, 109 (43), 20522-20528.*
Van Duyne et al. J Chem Phys 99 (3), Aug. 1, 1993, pp. 2101-2115.*
Carmona, P., "Vibrational spectra and structure of cystalline dipicolinic acid and calcium dipicolinate trihydrate," Spectrochimia Acta, 1979, 36A:705-712.
Carron et al., "Octadecylthiol-Modified Surgace-Enhanced Raman Spectroscopy Substrates: A New Method of the Detection of Aromatic Compounds," Environ. Sci. Tehnol., 1992, 26:1950-1954.
Chan et al., "Reagentless Identification of Single Bacterial Spores in Aqueous Soluction by Confocal Laser Tweezers Raman Spectroscopy," Anal. Chem., 2004, 76:599-603.
De Wit et al., "Application of a Polymerase Chain Reaction for the Detection of *Mycobacterium leprae* in Skin Tissues," J Clin Microbio, 1991, 29:906-910.
Dick et al., "Metal Film over Nanosphere (MFON) Electrondes for Surface-Enhanced Raman Spectroscopy (SERS): Improvements in Surface Nanostructure Stability and Suppression of Irreversible Loss," J Phys Chem B, 2002, 106:853-860.
Dieringer et al., "Surface enhanced Raman spectroscopy: new materials, concepts, characterization tools, and applications," Faraday Discuss, 2006, 132:9-26.
Driskell et al., "Low-Level Detection of Viral Pathogens by a Surface-Enhanced Raman Scattering Based Immunoassay," Anal Chem, 2005, 77:6147-6154.
Elam et al., "Viscous flow reactor with quartz crystal microbalance for thin film growth by atomic layer deposition," Rev Sci Instrum, 2002, 73:2981-2987.
Farquharson et al., Rapid Dipicolinic Acid extraction from *Bacillus*Spores Detected by Surgace-Enhanced Raman Spectroscopy, 2004, 58:351-354.
Fassanella et al., "PCR Assay to Detect *Bacillus anthracis* Spores in Heat Treated Specimens," J Clin Microbio, 2003, 41:896-899.
Goodacre et al., "Detection of the Dipicolinic Acid Biomarker in *Bacillus* Spores Using Curie-Poing Pyrolysis Mass Spectrometry and Fourier Transform Infrared Spectroscopy," Anal Chem, 72:119-127, published Jan. 1, 2000.
Haynes, C. L. and Van Duyne, R. P., "Plasmon-Sampled Surface-Enhanced Raman Excitation Spectroscopy," J Phys Chem B, 2003, 107:7426-7433.
Hulteen, J. C. and Van Duyne, R. P., "Nanosphere lithography: A materials general fabrication process for periodic particle array surfaces," J Vac Sci Tehnol A, 1995, 13:1553-1558.
Hurtle et al., "Detection of the *Bacillus anthracis* gyrA Gene by Using a Minor Groove Binder Probe," J Clin Microbio, 2004, 42:179-185.
Jarvis, R. M. and Goodacre, R., "Discrimination of Bacteria Using Surgace-Enhanced Raman Spectroscopy," Anal Chem, 2004, 76:40-47.
Jung, L. S. and Campbell, C. T., "Sticking Probabilities in Adsorption of Alkanethiols from Liquid Ethanol Solution onto Gold," J Phys Chem B, 2000, 104:11168-11178.
Jung, L. S. and Campbell, C. T., "Sticking Probabilities in Adsorption from Liquid Solutions: Alkylthiols on Gold," Physical Review Letters, 2000, 84:5164-5167.
King, In: Aluminum and its alloys, West, E G, Ed Ellis Horwood: New York, 1987; p. 313. Table of Contents Provided. Will provide specific pages at Examiner's request.

(Continued)

*Primary Examiner* — Jill Warden
*Assistant Examiner* — Julie Tavares
(74) *Attorney, Agent, or Firm* — Casimir Jones, S.C.

(57) ABSTRACT

The present invention relates to compositions, devices and methods for detecting microorganisms (e.g., anthrax). In particular, the present invention provides portable, surface-enhanced Raman biosensors, and associated substrates, and methods of using the same, for use in rapidly detecting and identifying microorganisms (e.g., anthrax).

8 Claims, 22 Drawing Sheets

(56) References Cited

OTHER PUBLICATIONS

King et al., "Performance Assessment of Three Commercial Assays for Direct Detection of *Bacillus anthracis* Spores," J Clin Microbiol, 2003, 41:3454-3455.

Litorja et al., "Surface-Enhanced Raman Scattering Detected Temperature Programmed Desorption: Optical Properties, Nanostructure, and Stability of Silver Film over SiO2 Nanosphere Surfaces," J Phys Chem B, 2001, 105:6907-6915.

McCreery, R. L. Raman Spectroscopy for Chemical Analysis; John Wiley & Sons: New York, 2000; vol. 157, p. 420. Table of Contents Provided. Will provide specific pages at Examiners request.

McFarland, A. D., "Using Nanoparticle Optics for Ultrasensative Chemical Detection and Surface-Enhanced Spectroscopy," Ph.D. Dissertation, Northwestern University, Dec. 2004.

McFarland et al., "Wavelength-Scanned Surface-Enhanced Raman Spectroscopy," J Phys Chem, 2005, 109:11279-11285.

Mosier-Boss, P. A. and Lieberman, S. H., "Detection of Nitrate and Sulfate Anions by Normal Raman Spectroscopy and SERS of Cationic-Coated, Silver Substrates," Applied Spectroscopy, 2000, 54:1126-1135.

Pelligrino et al., "Enhanced spore detection using dipicolinate extraction techniques," Analytica Chimica Acta, 2002, 455:167-177.

Ricca, E. et al., Eds, Bacterial Spore Formers: Probiotics & Emerging Applications, Horizon Scientific Press, p. 244. Table of Contents Provided. Will provide specific pages at Examiner's request. Published Nov. 2004.

Schatz, G. C. and Van Duyne, R. P., "Electromagnetic Mechanism of Surface-enhanced Spectroscopy," Surface-enhanced Vibrational Spectroscopy, John Wiley & Sons Ltd., 2002, 1:759-774.

Thompson et al., "Identification of Bacterial Spores Using Statistical Analysis of Fourier Transform Infrared Photoacoustic Spectroscopy Data," Applied Spectroscopy, 2003, 57:893-899.

Whitney et al., "Localized Surface Plasmon Resonance Nanosensor: A High-Resolution Distance-Dependence Study Using Atomic Layer Deposition," J Phys Chem B, 2005, 109:20522-20528.

Yolken, R. H. and Wee, S-B, "Enzyme Immunoassays in Which Biotinillated Beta-Lactamase is Used for the Detection of Microbial Antigens," J Clin Microbio, 1984, 19:356-360.

Yonzon et al., "A Glucose Biosensor Based on Surface-Enhanced Raman Scattering: Improved Partition Layer, Temporal Stability, Reversibility, and Resistance to Serum Protein Interference," Anal Chem, 2004, 76:78-85.

Zhang et al., "An electrochemical surface-enhanced Raman spectroscopy approach to anthrax detection," Proc. SPIE-Int. Soc. Opt.Eng., 2003, 5221:82-91.

Zhang et al., "Rapid Detection of an Anthrax Biomarker by Surface-Enhanced Raman Spectroscopy," J Am Chem Soc, 2005, 127:4484-4489.

\* cited by examiner

COMPOSITIONS, DEVICES AND METHODS FOR SERS AND LSPR

The present invention is a continuation-in-part of, and claims priority to, U.S. Provisional Patent Application Ser. No. 60/856,601, filed Nov. 3, 2006 and U.S. patent application Ser. No. 11/401,203, filed Apr. 10, 2006, which claims priority to U.S. Provisional Application Ser. No. 60/669,727, filed Apr. 8, 2005, each of which is incorporated herein by reference.

This invention was made with government support under DMR-0076097, DMR-0520519, DMR-0520513, EEC-0118025 and CHE-0414554 awarded by the National Science Foundation, under F49620-02-1-0381 awarded by the Air Force Office of Scientific Research MURI, and under DE-FG02-03ER15457 awarded by the U.S. Department of Energy. The government has certain rights in the invention. The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

The present invention relates to compositions, devices and methods for detecting microorganisms (e.g., anthrax). In particular, the present invention provides portable, surface-enhanced Raman biosensors, and associated substrates, and methods of using the same, for use in rapidly detecting and identifying microorganisms (e.g., anthrax).

BACKGROUND OF THE INVENTION

The rapid and accurate identification of bioagents is a vital task for first-responders in order to facilitate timely and appropriate actions in the event of a biological attack. *Bacillus anthracis*, a spore-forming bacterium and a dangerous pathogen for the disease anthrax, is an important example. *B. anthracis* bacteria exist in two different forms: rod-shaped organisms and spores. Rod-shaped organisms grow and divide in a nutrient rich environment. When the food supply is depleted, the organisms turn into spores that can survive for decades. Structurally, a spore consists of a central core cell surrounded by various protective layers. Calcium dipicolinate (CaDPA) exists in these protective layers and accounts for ~10% of the spore's dry weight (Bailey et al., 1965, J. Bacteriol. 89:984-987) therefore, it is a useful biomarker for *bacillus* spores (Goodacre et al., 2000, Anal. Chem. 72:119-127).

Among the potential biological warfare agent candidates, *B. anthracis* spores are of particular concern. First, they are highly resistant to environmental stress and are relatively easily produced into weapon-grade material outside the laboratory. Second, anthrax is an infectious disease, requiring medical attention within 24-48 h of initial inhalation of more than $10^4$ *B. anthracis* spores (Walt and Franz, 2000, Anal. Chem. 72:738 A-746A). However, the diagnosis of anthrax is not immediate because it takes 1-60 days for anthrax symptoms to appear in humans (Chin, 2000, Control of Communicable Diseases Manual; American Public Health Association: Washington, D.C., pp 20-25). Therefore, the rapid detection of *B. anthracis* spores in the environment prior to infection is an extremely important goal for human safety.

Thus, a great need exists for a rapid and sensitive detection protocol suitable for use by first responders to detect dangerous microorganisms (e.g., anthrax) that may be used in a biological attack. Furthermore, such materials and methods should be portable for use in the field at potential sites of exposure and capable of providing results on site in short order.

SUMMARY OF THE INVENTION

The present invention relates to compositions, devices and methods for detecting microorganisms (e.g., anthrax). In particular, the present invention provides portable, surface-enhanced Raman biosensors, and associated substrates, and methods of using the same, for use in rapidly detecting and identifying microorganisms (e.g., anthrax).

A rapid method and portable device suitable for use by first-responders to detect pathogenic bacteria, for example anthrax spores, using a low-cost, battery-powered, portable Raman spectrometer has been developed. The methods and devices of the present invention find use in the detection of a number of different analytes in a variety of different sample types. Preferred embodiments of the present invention find use for the detection of pathogens or components of pathogens. For example, *Bacillus subtilis* spores, harmless stimulants for *Bacillus anthracis*, were studied using surface-enhanced Raman spectroscopy (SERS) on silver film over nanosphere (AgFON) substrates. AgFON substrates are used for their mechanical robustness, SERS signal stability, and large SERS enhancement factors. These characteristics are important in the development of sensing technology, where reproducibility results with low sample-to-sample variation are of important. Calcium dipicolinate (CaDPA), a biomarker for *bacillus* spores, was efficiently extracted by sonication in nitric acid and rapidly detected by SERS. The presence of nitric acid from the digestion process additionally provides a convenient internal standard.

Improved binding efficiency of the CaDPA adsorption can be further accomplished by using atomic layer deposition (ALD) to coat the AgFON surface with a layer of alumina. The ALD technique permits the precise deposition of materials at Angstrom thicknesses. The alumina layer not only leads to an improvement in $K_a$ and more effective measurement, but also helps protect the underlying noble metal surface. In developing embodiments of the present invention, it was determined that the ALD technique provides a strategy for improving the stability of traditional SERS substrates. The shelf life of prefabricated substrates is at least 9 months prior to use (e.g., at least one year, more than three months, more than 6 months, etc.). In comparison to the bare AgFON substrates, the ALD modified AgFON substrates provide about twice the sensitivity with approximately six times shorter data acquisition time and approximately seven times longer temporal stability. As such, ALD expands the palate of available chemical methods to functionalize SERS substrates, which enable improved and diverse chemical control over the nature of analyte-surface binding for biomedical, homeland security, and environmental application.

AgFON surfaces optimized for 750 nm laser excitation have been fabricated and characterized by UV-vis diffuse reflectance spectroscopy and SERS. The SERS signal from extracted CaDPA was measured over the spore concentration range of $10^{-14}$-$10^{-12}$ M to determine the saturation binding capacity of the AgFON surface and to calculate the adsorption constant (Kspore=$1.7\times10^{13}$ M$^{-1}$). An 11 minute procedure is capable of achieving a limit of detection (LOD) of approximately $2.6\times10^3$ spores, below the anthrax infectious dose of $10^4$ spores. The data presented herein demonstrate that the shelf life of prefabricated AgFON substrates can be as long as 40 days prior to use. The sensing capabilities of the present invention can be successfully incorporated into a field-portable instrument. Using this technology, $10^4$ bacillus spores were detected with a 5 second data acquisition period on a one-month-old AgFON substrate. The speed and sensitivity of this SERS sensor indicate that this technology is useful for the field analysis of potentially harmful environmental samples.

One embodiment of the present invention is a portable device comprising a plurality of nanobiosensors configured for SERS detection of microorganisms. In some embodiments, the microorganisms are pathogenic bacteria. In some embodiments, the pathogenic bacteria can form spores. In some embodiments, the pathogenic bacteria are from the *Bacillus* genus, for example *B. anthracis*. In some embodiments, the portable device is capable of detecting less than $10^4$ microorganismal spores. Preferably, the portable device of the present intention is capable of detecting $2.6 \times 10^3$ spores of a microorganism. In some embodiments, the device of the present invention is capable of detecting more than $2.6 \times 10^3$ spores of a microorganism. In some embodiments, the portable device is hand held. In some embodiments, the portable device further comprises a laser excitation power of approximately 50 mW, although the present invention is not so limited.

One embodiment of the present invention comprises a portable device wherein the nanobiosensors of the device comprise nanosphere substrates. In some embodiments, the nanosphere substrates are coated with a noble metal. In some embodiments, the noble metal used to coat the nanosphere substrates is silver. In some embodiments, the silver coated nanosphere substrates are further coated with alumina. In some embodiments, the nanosphere substrates are optimized for 750 nm laser excitation.

One embodiment of the present invention comprises a method of detecting the presence or absence of a microorganism in a sample, comprising: contacting a sample suspected of containing a microorganism with a portable device comprising a plurality of nanobiosensors configured for SERS and detecting the presence or absence of the suspected microorganism by detecting a signal generated from said portable device. In some embodiments, the microorganism being tested for is a pathogenic bacterium. In some embodiments, the pathogenic bacterium is a spore forming bacteria, such as *B. anthracis*.

DEFINITIONS

Figure 1:
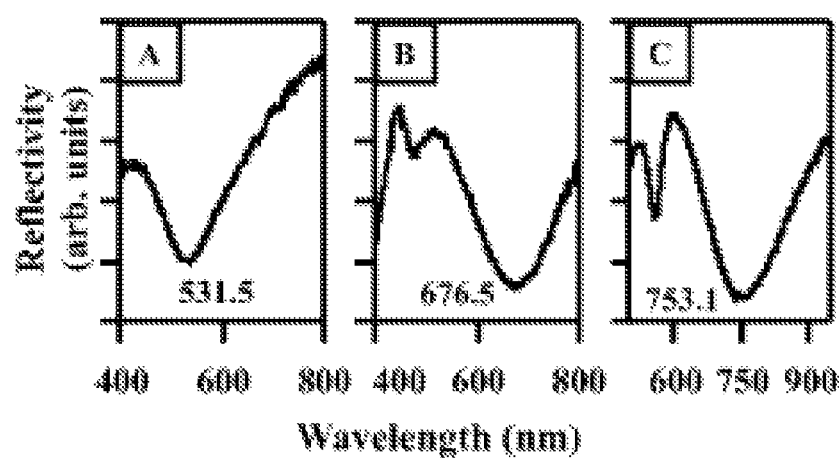
FIG. 1. UV-vis diffuse reflectance spectra of different AgFON substrates in air. (A) D=390 nm, dm=200 nm; (B) D=510 nm, dm=200 nm; and (C) D=600 nm, dm=200 nm.

As used herein, the term "nanobiosensors configured for surface enhanced Raman spectroscopy detection of an analyte" refers to any small sensor configured to fit within a hand-held device that is specific for detection of one or more analytes, and is capable of having an altered surface enhanced Raman signal in the presence of the specific analyte(s). In preferred embodiments, the nanobiosensors comprise components for specifically, but reversibly, interacting with the specific analyte.

As used herein, the term "surface bound reversibly-binding receptor" refers to a receptor bound to the surface of a nanobiosensor of the present invention that binds reversibly to a specific analyte. In preferred embodiments, the interaction of the receptor and the analyte lasts long enough for detection of the analyte by the sensor.

As used herein, the term "self-assembled monolayer" refers to a material that forms single layer or multilayers of molecules on the surface of a nanobiosensor.

As used herein, the term "nanowell" refers to a solid surface comprising wells for immobilizing the nanobiosensors of the present invention. In preferred embodiments, the nanowells are made of an inert material and are large enough to hold a plurality of nanobiosensors.

As used herein, the term "analyte" refers to any molecule or atom or molecular complex suitable for detection by the nanobiosensors of the present invention. Exemplary analytes include, but are not limited to, various biomolecules (e.g., proteins, nucleic acids, lipids, etc.), pathogens, glucose, ascorbate, lactic acid, urea, pesticides, chemical warfare agents, pollutants, and explosives.

As used herein, the term "a device configured for the detection of surface enhanced Raman scattering signal from said nanobiosensors" refers to any device suitable for detection of a signal from the nanobiosensors of the present invention. In some embodiments, the device includes delivery and collection optics, a laser source, a notch filter, and detector.

As used herein, the term "spectrum" refers to the distribution of electromagnetic energies arranged in order of wavelength.

As used the term "visible spectrum" refers to light radiation that contains wavelengths from approximately 360 nm to approximately 800 nm.

As used herein, the term "ultraviolet spectrum" refers to radiation with wavelengths less than that of visible light (i.e., less than approximately 360 nm) but greater than that of X-rays (i.e., greater than approximately 0.1 nm).

As used herein, the term "infrared spectrum" refers to radiation with wavelengths of greater than 800 nm.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as bacteria, surface matter, soil, water, crystals and industrial samples. Such examples are not however to be construed as limiting the sample types applicable to the present invention.

As used herein, the term "medium" refers to the fluid environment of an analyte of interest. In some embodiments, the medium refers to a bodily fluid. The bodily fluid may be, for example, blood, plasma, serum, cerebrospinal fluid, vitreous or aqueous humor, urine, extracellular fluid, or interstitial fluid. In some embodiments, the medium is an in vivo medium. In other embodiments, the medium is an ex vivo or in vitro medium, for example, a fluid sample taken from a subject. In other embodiments, the medium is a liquid that is found on the surface of an object or structure, wherein which a bacteria or other biological organism (e.g., pathogen) is present or expected to be present.

As used herein, the term "pathogen" refers or an agent that can cause disease in other organisms or in humans, animals and plants (e.g., bacteria, viruses, or parasites). Examples of pathogens of the present invention include microorganisms capable of causing damage or harm to a living organism. For example, *B. anthracis* is a pathogen capable of causing anthrax in humans and non-human animals, and is considered a biological weapon.

DETAILED DESCRIPTION OF THE INVENTION

A rapid method and portable device suitable for use by first-responders to detect pathogenic bacteria, for example anthrax spores, using a low-cost, battery-powered, portable Raman spectrometer has been developed.

Certain illustrative embodiments of the invention are described below. The present invention is not limited to these embodiments.

The localized surface plasmon resonance (LSPR) wavelength shift response, $\Delta\lambda_{max}$, of silver (Ag) nanoparticles fabricated by nanosphere lithography (NSL) has been used to develop a new class of nanoscale optical biosensors. On the most elementary level, the LSPR wavelength shift response of these sensors is understood using a model of the refractive-index response of propagating surface plasmons on a planar noble metal surface:

$$\Delta\lambda_{max}=m\Delta n[1-\exp(-2d/l_d)], \quad (I)$$

where $\Delta\lambda_{max}$ is the wavelength shift, m is the refractive-index sensitivity, $\Delta n$ is the change in refractive index induced by an adsorbate, d is the effective adsorbate layer thickness, and $l_d$ is the characteristic electromagnetic field decay length. This model assumes a single exponential decay of the electromagnetic field normal to the planar surface, which is accurate for a propagating surface plasmon, but is undoubtedly an oversimplification for the electromagnetic fields associated with noble metal nanoparticles. While this oversimplified model does not quantitatively capture all aspects of the LSPR nanosensor response, it does provide guidance for sensor optimization. In particular, Equation (1) highlights the importance of distance dependence as described by the electromagnetic field decay length, $l_d$.

In developing embodiments of the present invention, the long range distance dependence of the LSPR nanosensor was explored using self-assembled monolayers (SAMs) of 11-mecaptoundecanoic acid (11-MUD) and $Cu^{2+}$ ions fabricated on arrays of noble metal nanoparticles with various sizes, shapes, and compositions. The spatial resolution as limited to the thickness of the 11-MUD/$Cu^{2+}$ monolayer that was at least 1.6 nm. Several interesting characteristics of the long-range behavior were found including, but not limited to: (1) the LSPR $\lambda_{max}$ shift vs. SAM thickness is nonlinear; (2) Ag nanoparticles are more sensitive than Au nanoparticles; (3) nanotriangles have larger sensing distances than nanohemispheroids; (4) increasing the nanoparticle in-plane width results in larger sensing distances; and (5) decreasing nanoparticle out of-plane height results in larger sensing distances. It has been shown that semi-quantitative theoretical calculations revealed that the plasmon resonance shift is controlled by the average electromagnetic field over the nanoparticle surface. Similarly, the short range distance dependence (0-3 nm) of the LSPR nanosensor has been studied using alkanethiol, $CH_3(CH_2)_xSH$ (x=2-11, 13-15, and 17), monolayers. It was found that Equation 1 accounts for the short range LSPR response if one assumes a value $l_d$=5-6 nm. In addition, the dependence of $\Delta\lambda_{max}$ on the chain length of the alkanethiol monolayer was found to be linear, with a large slope of 3.1-3.3 nm per $CH_2$ unit.

Even though much information was obtained from these previous long and short range distance dependence studies, it was contemplated that new information could be obtained if it were possible to deposit single layers of a material with thicknesses of approximately 1 Å. Furthermore, while the refractive index of the bulk SAM molecule is known, the refractive index of the SAM is not known, making an accurate theoretical model of the experiment difficult. In developing embodiments of the present invention, it was found that atomic layer deposition (ALD) is a fabrication method that produces highly uniform and controlled thin films. Precursor gases are alternately pulsed through the reactor and purged away resulting in a self-limiting growth process that constructs a film one monolayer at a time. Highly uniform monolayers of $Al_2O_3$ are deposited with an approximately 1 Å thickness resolution and a refractive index of 1.57. As such, depositing $Al_2O_3$ multilayers onto a noble metal nanosensor allows the long range distance dependence of the LSPR nanosensor to be probed with 10× spatial resolution compared with alternative methods. Additionally, the nucleation and growth of $Al_2O_3$ on Ag surfaces was examined using quartz crystal microbalance (QCM), variable angle spectroscopic ellipsometry (VASE), and X-ray photoelectron spectroscopy (XPS) measurements.

Figure 14:
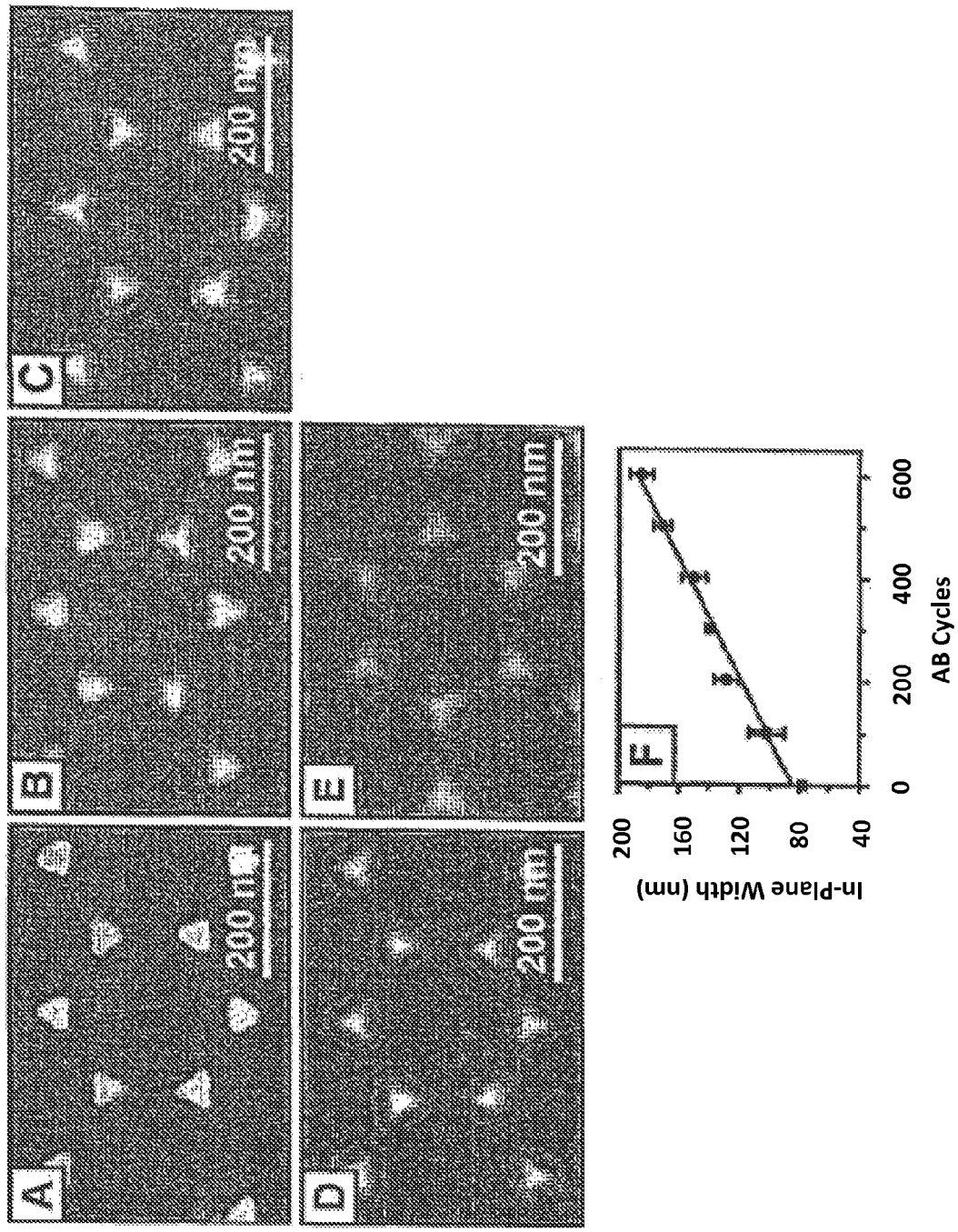
FIG. 14. SEM images of (A) bare Ag nanopaticles (a=90 nm, b=51 nm) and Ag nanoparticles following (B) 100, (C) 200, D) 400, and (E) 600 AB cycles of $TMA/H_2O$. (F) Plot of in-plane width of Ag nanoparticle AB cycles determined from the SEM images.

In developing embodiments of the present invention, SEM images of bare and $Al_2O_3$ coated Ag nanotriangles on Si were acquired. Si (111) was chosen as the substrate to minimize charging and to produce high quality images. Nanoparticles fabricated on Si substrates are similar to those fabricated on glass substrates. FIG. 14 presents SEM images of bare Ag nanoparticles (FIG. 14A) and Ag nanopaticles coated by $Al_2O_3$ ALD using 100 (FIG. 14B), 200 (FIG. 14C), 400 (FIG. 14D), and 600 (FIG. 14E) AB cycles. FIG. 14F depicts a plot of the nanoparticle in-plane width vs. AB cycles determined from the SEM images and yields a growth rate of 0.9 Å/cycle.

Figure 2:
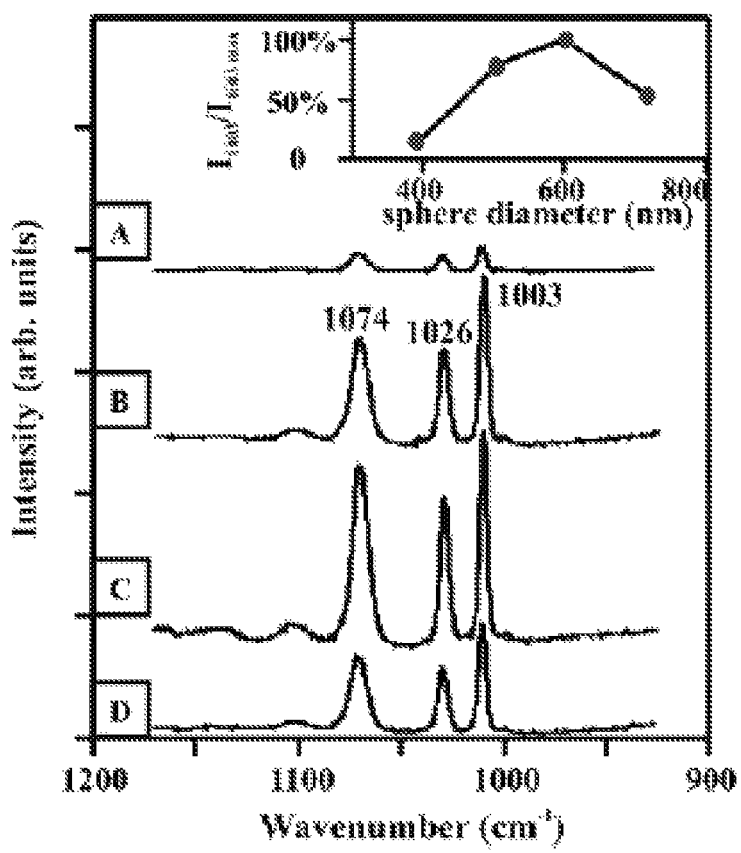
FIG. 2. SERS spectra of 20 µL, 1 mM benzenethiol in ethanol on different AgFON substrates. (A) D=390 nm, dm=200 nm; (B) D=510 nm, dm=200 nm; (C) D=600 nm, dm=200 nm; and (D) D=720 nm, dm=200 nm. The inset shows the variation of the benzenethiol SERS intensity ratio (I1003/I1003, max) with sphere sizes. I1003, max is taken from spectrum 2C. For all spectra, $\lambda$ex=750 nm, Pex=3 mW, acquisition time=1 min.
Figure 15:
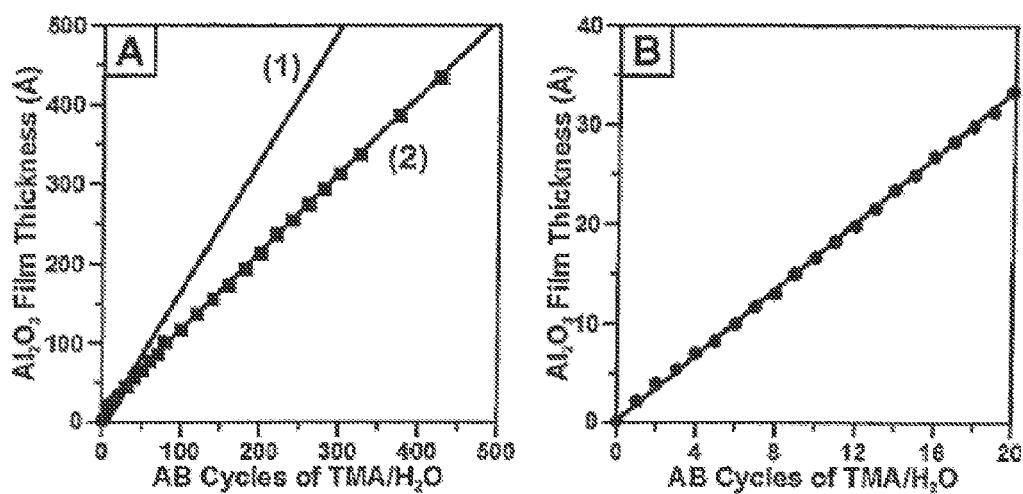
FIG. 15. Ellipsometry measurements for $Al_2O_3$ ALD grown on a 50 nm Ag film. (A) Ellipsometry data for 0-425 AB cycles of TMA and water. Circles denote single AB cycles of TMA and water and squares denote multiple AB cycles of TMA and water. (B) Ellipsometry data for 0-20 AB cycles TMA and water. Circles denote single AB cycles of TMA and water. Growth rate for 0-20 AB cycles (1)=1.65 Å per cycle. Growth rate for 30-425 AB cycles (2)=0.98 Å per cycle.

VASE studies were carried out to accurately monitor the $Al_2O_3$ film thickness and growth rate. Measurements were carried out on a 50 nm Ag film e-beam deposited on glass. FIG. 15 demonstrates the $Al_2O_3$ film thickness vs. AB cycles of TMA and water deposited on an Ag-coated Si surface measured with VASE. VASE data is presented for 0-425 AB cycles (FIG. 15A). Two growth rates were observed: growth rate for 0-20 AB cycles=1.65 Å per cycle (FIG. 15A-1) and the growth rate for 20-425 AB cycles=0.98 per cycle (FIG. 15A-2). FIG. 15B depicts the VASE data for just the 0-20 AB cycles. Both growth rates are linear, respectively and can therefore be predicted and controlled. The higher growth rate (1.65 Å per cycle) measured during the first 20 AB cycles is a consequence of much larger $H_2O$ exposures resulting from removing the sample from the reaction chamber and exposing the sample to room air after each AB cycle to collect an extinction spectrum. The $Al_2O_3$ ALD growth rate increases with increasing water. The growth rate then seduces to approximately 0.98 Å per cycle once multiple AB cycles of TMA and water are employed (FIG. 15A-2). This growth rate is very close to the value determined from the SEM measurements (FIG. 14F) and is typical for ALD $Al_2O_3$ on hydroxylated SiO, under these conditions.

Figure 16:
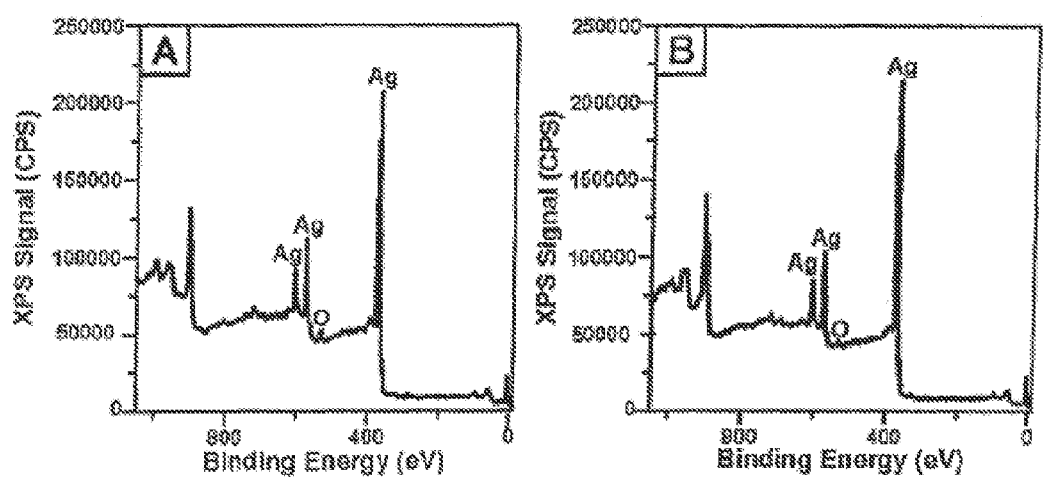
FIG. 16. XPS measurements on 50 nm Ag film. (A) XPS measurements taken on the Ag film as deposited. 10.5% oxygen was found on the Ag film surface. (B) XPS measurements taken on the Ag film after annealing for 40 minutes under UHV at approximately 200° C. 5.6% oxygen was on the Ag film surface.

As $Al_2O_3$ ALD growth mechanism is correlated with surface hydroxyl groups, it was surprising that the $Al_2O_3$ AL.D proceeds at the same rate on Ag as on hydroxylated SiO, without apparent inhibition or nucleation delay. Hydroxyl groups may be present if the Ag surface is oxidized, however VASE detected no AgO before or after the $Al_2O_3$ ALD. Further, measurements were made using XPS, an extremely sensitive probe for surface composition. XPS was performed on a 50 nm Ag film e-beam deposited on glass. FIG. 16 presents XPS measurements on a 50 nm Ag film e-beam deposited on glass obtained before (FIG. 16A) and after (FIG. 16B) annealing the Ag film at approximately 200° C. for 40 min. FIG. 16A shows 10.5% oxygen content on the surface of the Ag film. After annealing the substrate the oxygen content on the Ag film surface drops to 5.6% (FIG. 16B). The oxygen XPS peak does not appear at the expected position for AgO (−528-532 eV) indicating that the oxygen peak results from surface impurities.

Figure 17:
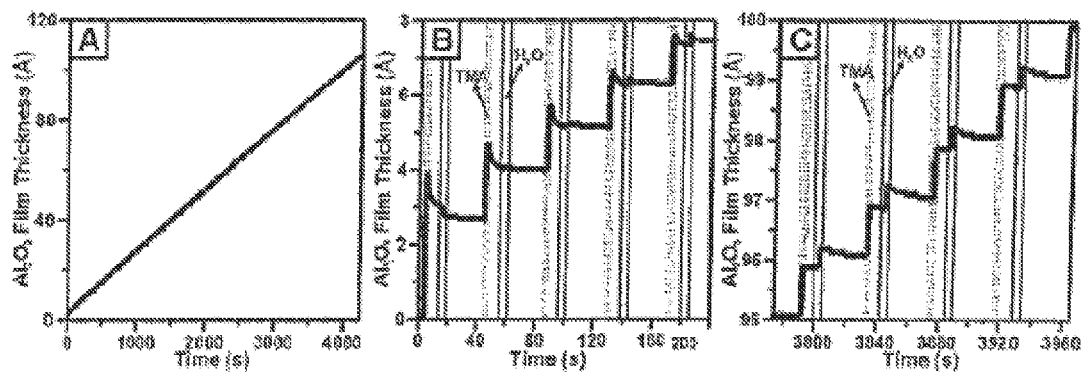
FIG. 17. Plots of $Al_2O_3$ growth rate and QCM step ratio vs. AB cycles of TMA and water measured with QCM on 50 nm Ag film. (A) QCM measurements for 0-100 AB cycles of TMA and water. (B) QCM measurements for the first 5 AB cycles of TMA and water. (C) QCM measurements for the final AB cycles of TMA and water. 50 nm Ag was deposited on the QCM to insure similar experimental environment. The shaded areas represent the time periods that the TMA and water dosing valves were open.

In developing embodiments of the present invention, further exploration of the $Al_2O_3$ growth mechanism on Ag was done by QCM studies (FIG. 17). QCM measurements were conducted on 50 nm Ag film e-beam deposited directly on the QCM crystal. FIG. 17A shows the QCM measurements recorded during 100 AB cycles of $Al_2O_3$ ALD. The QCM signals were converted to $Al_2O_3$ thickness assuming a density of 2.6 g/cm$^3$. The $Al_2O_3$ growth is linear with a growth rate of 1.0 Å/cycle in agreement with the VASE and SEM results. Moreover, there is no indication of inhibited initial growth as expected for $Al_2O_3$ ALD on a noble metal surface. The steplike structure in FIG. 17A reflects the discrete mass changes produced by the individual TMA and $H_2O$ exposures. Expanded views of the QCM data at early and late times are given in FIGS. 17B and 17C, respectively. The shaded areas represent the time periods that the TMA and water dosing valves were open. The QCM structure in FIG. 17B reveals details about the mechanism for $Al_2O_3$ nucleation and growth on Ag. FIG. 17B shows a large thickness change of 3-4 Å during the first TMA exposure. Given that XPS and VASE detect no AgO and little surface oxygen, it is contemplated that the TMA reacts directly with the Ag.

During the initial $Al_2O_3$ ALD cycles on Ag, the thickness decreases during the TMA purge periods (FIG. 17B). It is contemplated that this decrease in thickening results from the desorption of physiosorbed $H_2O$ or the recombinative desorption of surface OH groups. There is a net thickness decrease following the $H_2O$ doses and purges at early times (FIG. 17B) and a net thickness increase at later times (FIG. 17C). This net change reflects the density of surface OH groups, wherein larger net increases result from larger OH group coverages. The net thickness change is negative in FIG. 17B because there are no OH groups on the metallic Ag surface. However, the net thickness change is positive (FIG. 17C) because the ALD $Al_2O_3$ surface is fully hydroxylated at 50° C. It was determined that approximately 20 AB cycles are required for the net thickness to reach the steady-state value shown in FIG. 17C.

Figure 18:
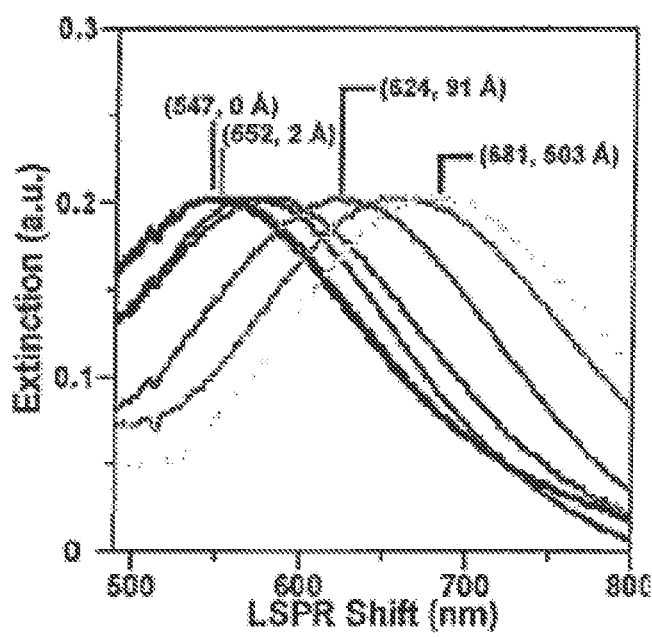
FIG. 18. LSPR spectroscopy of Ag nanoparticles (a=90 nm, b=40 nm) for 0-450 AB cycles of TMA and water.

FIG. 18 depicts exemplary LSPR extinction spectra for triangular Ag nanoparticles with an in-plane width (a) of 90 nm and out-of-plane height (b) of 40 nm. The UV-vis spectra for Ag nanoparticles with 0-450 cycles of TMA and water is presented in FIG. 18. As subsequent ALD $Al_2O_3$ layers are completed, the LSPR $\lambda_{max}$ position red shifts, which is consistent with previous work. Importantly, these results demonstrate that the LSPR nanosensor has sensitivity to detect the deposition of each successive $Al_2O_3$ monolayer. For nanoparticles with a=90 nm and b=40 nm a 5 nm LSPR $\lambda_{max}$ shift is observed with 2 Å of $Al_2O_3$. Furthermore, it is possible to detect sub-monolayers of material ALD of $Al_2O_3$ thereby allowing for the fabrication of Angstrom thick monolayers and providing a 10× increase in the spatial resolution compared to previous work.

Figure 3:
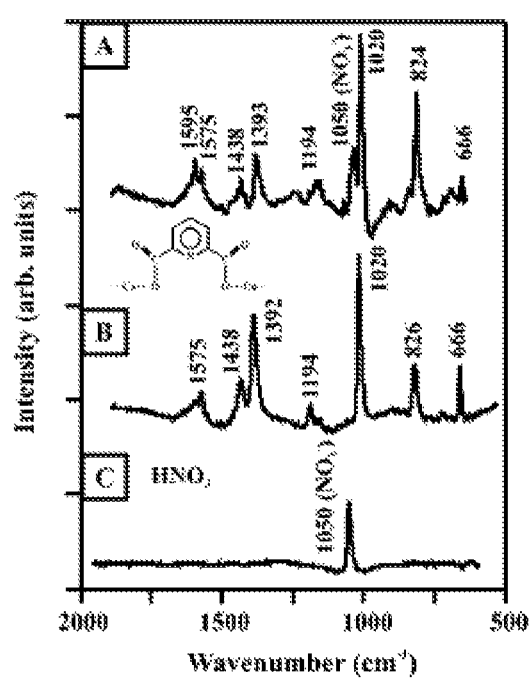
FIG. 3. (A) SERS spectrum of $3.1 \times 10^{-13}$ M spore suspension ($3.7 \times 10^4$ spores in 0.2 µL, 0.02 M $HNO_3$) on an AgFON substrate. (B) SERS spectrum of $5.0 \times 10^{-4}$ M CaDPA. (C) SERS spectrum of 0.2 µL of 0.02 M $HNO_3$; $\lambda$ex=750 nm, Pex=50 mW, acquisition time=1 min, D=600 nm, dm=200 nm.
Figure 19:
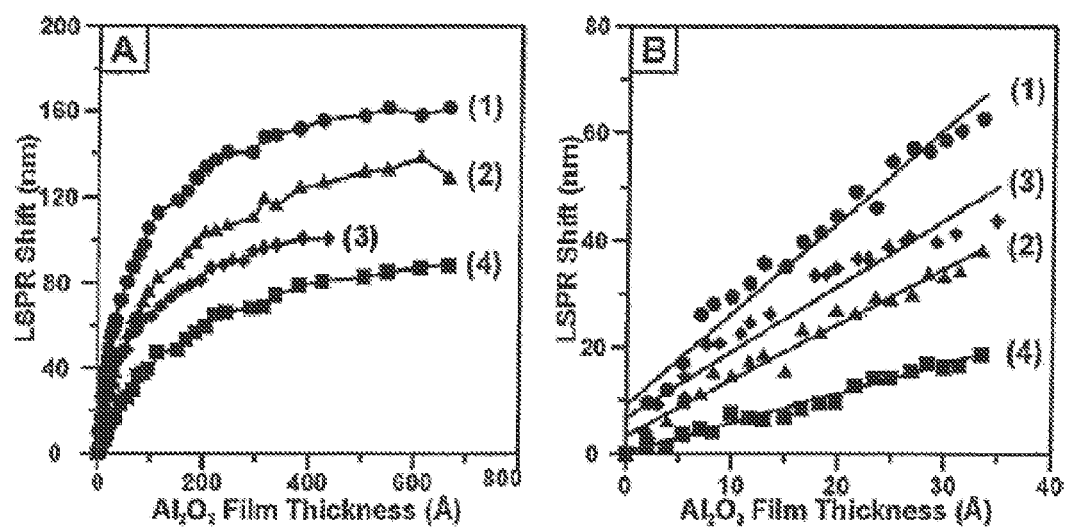
FIG. 19. Demonstration of LSPR shifts vs. $Al_2O_3$ film thickness. (A) Out-of plane height dependence on the long and short range distance dependence for Ag triangular nanoparticles a=90 nm and b=(1) 30 nm, (2) 40 nm, and (4) 51 nm and Ag hemispherical nanoparticles a=104 nm and b=52 nm (3). Data presented for 0-600 AB cycles of TMA and water. (B) Out-of-plane height dependence of the short range distance dependence for the Ag triangular nanoparticles a=90 nm and b=(1) 30 nm, (2) 40 nm, and (4) 51 nm and Ag hemispherical nanoparticles a=104 and b=52 nm (3). Data presented for 0-20 AB cycles of TMA and water. Linear regression was used to fit the data to lines described by the following equations: y=1.7x+9.1; $R^2$=0.9602 (1), 1.0x+3.5; $R^2$=0.9689 (2) 1.2x+7.0; $R^2$=0.9293 (3), and y=0.5x+0.1; $R^2$=0.9744.

FIG. 19 depicts plots of the LSPR $\lambda_{max}$ shift vs. $Al_2O_3$ film thickness for triangular nanoparticles with a=90 nm and b=30 nm (1), 40 nm (2), 51 nm (4), and hemispheroidal nanoparticles with a=104 nm and b=54 nm (3). In FIG. 19A the LSPR $\lambda_{max}$=shift vs. $Al_2O_3$ film thickness response is shown for 0-600 AB cycles. At short distances from the nanoparticle surface, the LSPR $\lambda_{max}$ shift follows a linear slope, but as the distance from the nanoparticle increases, the curve bends over, and eventually levels off once the nanoparticle has reached its saturation point. As the nanoparticle height decreases and the in-plane width remains constant, the LSPR $\lambda_{max}$ shift increases. The short range distance dependence is highlighted in FIG. 19B which depicts the $\lambda_{max}$ shift vs. $Al_2O_3$ film thickness response for the first 0-20 AB cycles. After each cycle a LSPR extinction spectrum was collected which presents a highly detailed view of the short range distance dependence of the LSPR nanosensor. Because $Al_2O_3$ layers deposited by ALD are approximately 1.1 Å in thickness this is the first time that a detailed picture of both the short and long range distance dependences of the LSPR nanosensor have been obtained in a single integrated experiment. In fact, the results show that at short distances from the nanoparticle surface, the LSPR $\lambda_{max}$ shift vs. layer thickness follows a steep linear trend compared with the moderate slope at larger distance from the nanoparticle surface. Nanoparticles with fixed in-plane widths and decreasing out-of-plane heights yield larger sensing distances (FIG. 19B-1) as has been observed at larger distances from the nanoparticle surface. Previous results have shown that hemispheroidal nanoparticles have a smaller sensing distance than triangular nanoparticles of similar volume. However, FIG. 19B-3 shows that the exemplary hemispheroidal particles (a=104 nm and b=52 nm) have a larger LSPR $\lambda_{max}$ shift at long distances compared with triangular nanoparticles with a=90 nm and b=51 nm (FIG. 17 A-4). Also, at short distances from the nanoparticle surface, the hemispheroidal particles have larger LSPR $\lambda_{max}$, shifts than both triangular nanoparticles with a=90 and b=39 nm and 51 nm.

Figure 20:
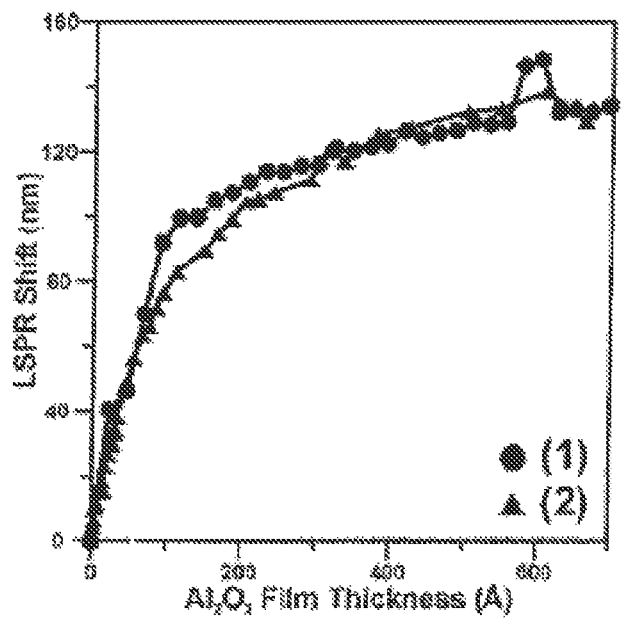
FIG. 20. Comparison of calculated (1) and experimental (2) shift of the LSPR from bare truncated tetrahedral particles with a=90 nm and b=40 nm.

Using discrete dipole approximation (DDA), the LSPR $\lambda_{max}$ shift measurements for silver particles coated with multilayers of $Al_2O_3$ were measured. In this method, the particle and $Al_2O_3$ coating are represented using a cubic grid of polarizable elements, with the polarizability of each element determined by the local dielectric constant. The particles are represented either as a truncated tetrahedron or as a hemispheroid, with dimensions taken to match the experimental results. The grid size in these calculations is 2 nm and the wave vector is taken perpendicular to the bottom surfaces of the truncated tetrahedron or hemispheroid. The refractive index of silver is taken from Hunter and Lynch (1985, Handbook of Optical Constants of Solids, Academic Press, New York) and that for the adsorbate $Al_2O_3$ is taken to be 1.57 from experimental data. The resonance wavelength of the truncated tetrahedron shaped silver particles was calculated with the layer thickness of the $Al_2O_3$ taken to be the grid size, 2 nm. This is not the same as the layer thickness of $Al_2O_3$, however, the dependence of the LSPR $\lambda_{max}$ shifts on the layer thickness are not sensitive to this difference for layers that are more than around 5 nm thick (as demonstrated in FIG. 20). FIG. 20 shows excellent agreement between the experimental and calculated results for the truncated tetrahedral shapes. These results are similar to those obtained in previous work involving the long range dependence of the LSPR $\lambda_{max}$ shifts using 11-MUD/Cu2+ multilayers, but herein the index of refraction of the $Al_2O_3$ is known, whereas with the SAM multilayers it could only be estimated. The only significant differences between theory and experiment in FIG. 20 are (1) that the theory shift is higher than experiment for layer thicknesses of 10-30 nm, and (2) a small bump in the calculated result at 50 nm. It is contemplated that the 10-30 nm result arises from small differences between theory and experiment in the precise definition of the layer structure. It is further contemplated that the bump is a photonic resonance effect that is extremely sensitive to layer structure and thus unlikely to show up in the same way in the experiment.

Figure 21:
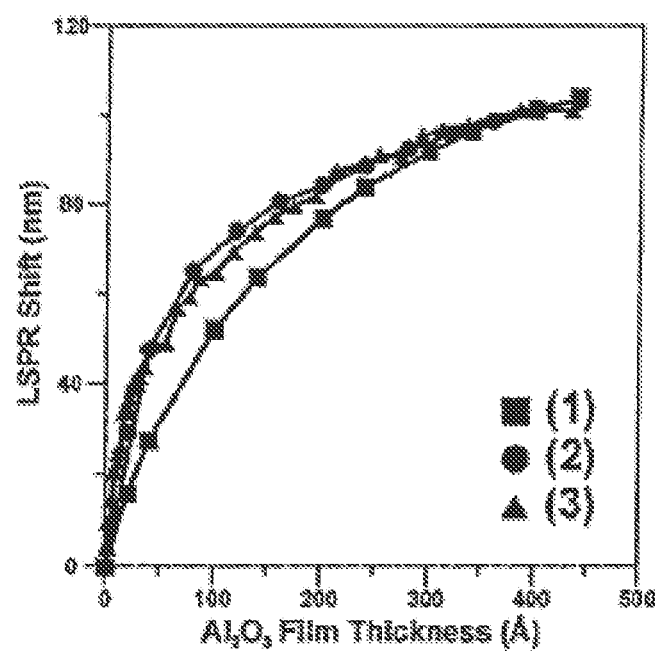
FIG. 21. Experimental (●) vs. calculated (■) shift of the LSPR from bare hemispheroidal particles with a=102 and b=54 nm along with experimental results (▲).
Figure 22:
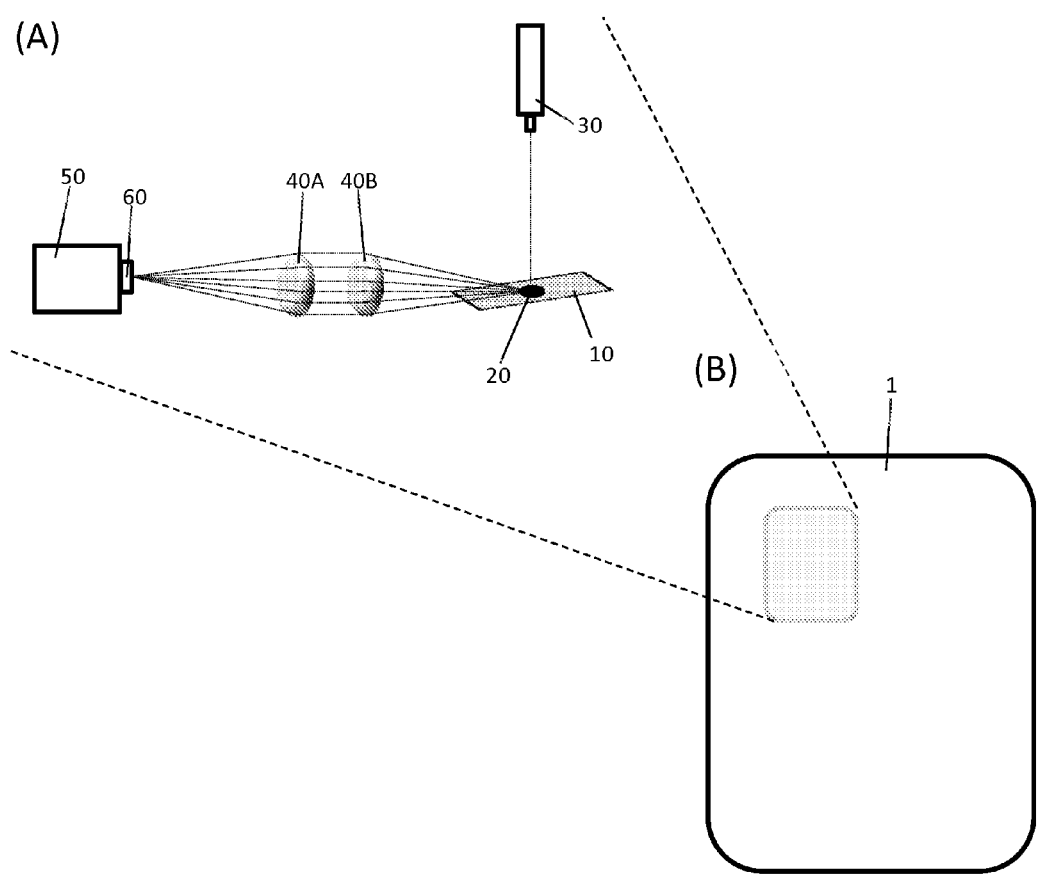
FIG. 22. Schematic of a portable device consistent with some embodiments of the invention. (A) An exemplary exterior of a portable device 1. (B) An exemplary interior view of a portable device depicts a laser source 30, sensing platform 10 (comprising alumina-modified AgFON substrate), target analyte 20, collection optics 40, notch filter 60, and detector 50.

The hemispheroidal nanoparticle was modeled using the same parameters as the triangular nanoparticle. Initially, the hemispheroidal nanoparticle was modeled as half an ellipsoid with dimensions: diameter—=104 nm and height=52 nm. The nanoparticle was coated with layers of $Al_2O_3$. The calculated results as well as the LSPR $\lambda_{max}$ shifts from the experiment are presented in FIG. 21. This demonstrates, as noted earlier; that the measured LSPR $\lambda_{max}$ red shifts sharply with increasing $Al_2O_3$ film thickness for layer thicknesses less than 10 nm and then bends over as the thickness is increased. However, the calculations show that the LSPR $\lambda_{max}$ red shifts almost linearly with increasing $Al_2O_3$ layer thickness, with a slope that is significantly smaller than is observed. Thus it seems that even though the particle was modeled using the exact shape parameters from the experiment, the model does not describe the observed sensitivity to layer thickness. Further, the difference between theory and experiment is consistent with the presence of a short range near-field around the hemispheroidal particle, such as would arise from small radius of curvature features such as the sharp points that are present in the truncated tetrahedral structure. As such, it is contemplated that the idealized hemispheroidal shape does not characterize the annealed particle completely, and there exist additional sharp features, not resolvable with AFM, that produce the short range near-field behavior that is seen. To model this, it is assumed that at the bottom edge of each spheroid, these exists an "apron" of metal that arises from wetting the substrate during the annealing stage, or a crack located under each structure. Thus the hemispheroidal nanoparticle is surrounded by a ring of metal that is 8 nm in width and 4 nm in height whose bottom surface is parallel to the bottom surface of the hemispheroid. The results of DDA calculations with this structure (FIG. 21) agree well with the experimental LSPR $\lambda_{max}$ shifts. As such it is demonstrated that a small, sharp feature on the nanoparticle can have a large influence on the near-field, and hence on the short-range dependence on layer thickness. This influence becomes less important when the layer thickness is increased, especially when the layer thickness is larger than 30 nm.

In the last two decades, various biological and chemical techniques have been developed to detect bacillus spores. Two important biological methods are the polymerase chain reaction (PCR) (De Wit et al., 1991, J. Clin. Microbiol. 29:906-910; Hurtle et al., 2004, J. Clin. Microbiol. 42:179-185; Fasanella et al., 2003, J. Clin. Microbiol. 41:896-899) and immunoassays (Yolken and Wee, 1984, J. Clin. Microbiol. 19:356-360; King et al., 2003, J. Clin. Microbiol. 41:3454-3455). PCR, a primer-mediated enzymatic DNA amplification method, requires expensive reagents, molecular fluorophores, and considerable sample processing prior to analysis. The limit of detection (LOD) based on PCR detection of bacterial pagA gene is $\times 10^3$ spores in 3 h. Immunoassays, which rely on the interaction between antibodies and B. anthracis cell surface antigens, can detect $10^5$ spores in 15 min. However, in immunoassays, it is necessary to employ specific antibodies for the desired agents and to individually adjust the mobile-phase conditions for their capture, elution, and separation.

Recently, relatively rapid chemical methods for the detection of *bacillus* spores have been developed. For instance, photoluminescence detection based on the formation of terbium (Tb(III)) dipicolinate was found to have a LOD of 103 *B. subtilis* colony-forming-units $mL^{-1}$ in 5-7 min. (Pellegrino et al., 2002, Anal. Chim. Acta 455:167). This method compares the enhanced luminescence of the terbium dipicolinate complex to Tb(III) alone. However, an increase in the luminescence intensity can also occur by the complexation of Tb(III) with aromatic compounds other than dipicolinic acid (Beltyukova et al., 1986, Dokl. Akad. Nauk. 291:1392-1395). Due to the frequency of false positives and its limited ability for target analyte identification, alternative approaches with improved selectivity would be a welcome addition to the arsenal of anthrax detection methods.

Compared to photoluminescence, vibrational spectroscopy possesses highly specific chemical information content and, therefore, is capable of uniquely identifying target analytes. Both Fourier transform infrared (FT-IR) (Thompson et al., 2003, Appl. Spectrosc. 57:893-899) and Raman (Jarvis and Goodacre, 2004, Anal. Chem. 76:40-47; Chan et al., 2004, Anal. Chem. 76:599-603) spectroscopies have demonstrated the ability to discriminate among different bacterial spores. However, the implementation of near infrared (NIR) and mid-infrared spectroscopies has fundamental limitations due to the competitive absorption of water and inherent spectral congestion. In contrast, Raman spectroscopy is well-suited to applications in aqueous environments because of the small Raman scattering cross section of water (McCreery, R. L. Raman Spectroscopy for Chemical Analysis; John Wiley & Sons: New York, 2000; Vol. 157, p 420; also see, e.g., U.S. Pat. App. No. 20040180379). Recently, for example, single bacterial spores have been detected using micro-Raman spectroscopy. As a consequence of different individual sporulations, however, the micro-Raman spectra vary significantly from one spore to another. Additionally, the applications that require complex instrumentation used in this approach restrict its applicability in field-portable measurements. The detection of *bacillus* spores by normal Raman spectroscopy (NRS) has also been demonstrated (Farquharson et al., 2004, Raman Spectrosc. 35:82-86), however, NRS suffers from low sensitivity, so that long data acquisition times (5-13 min) and high laser powers (400 mW) are required. In comparison, surface-enhanced Raman spectroscopy (SERS) yields more intense Raman signals at much lower laser excitation power. SERS produces very large enhancements in the effective Raman cross section of species spatially confined within the electromagnetic fields generated by excitation of the localized surface plasmon resonance (LSPR) of nanostructured noble metal surfaces (Schatz et al., Electromagnetic Mechanism of Surface-Enhanced Spectroscopy. In Handbook of Vibrational Spectroscopy; Chalmers, J. M., Griffiths, P. R., Eds.; Wiley: New York, 2002; Vol. 1, pp 759-774). The SERS signals of ensemble-averaged molecules show enhancements up to 8 orders of magnitude over NR signals (Haynes and Van Duyne, 2003, J. Phys. Chem. B 107:7426-7433). Furthermore, the low power required by SERS allows the development of a compact, field-portable detection system.

Calcium dipicolinate (CaDPA) is a component of the bacterial spore case. The process of sporogenesis occurs when the vegetative bacterial cell segregates its contents to form a sporangium. The sporangium content includes what will be the future bacterial spore, also known as an endospore. Upon sporogenesis, the water is completely removed from the endospore by the sporangium, which is then covered by a cortex layer rich in calcium dipicolinate. CaDPA can be a major component of the spore case. In fact, CaDPA can comprise 5-20% of the spore case, with the concentration varying among different genera and species of spore forming bacteria.

Accordingly, the present invention provides compositions and methods for the rapid extraction of CaDPA from *B. subtilis* spores, stimulants for *B. anthracis* spores, and SERS detection on reproducible (Dick et al., 2002, J. Phys. Chem. B 106:853-860), stable (Zhang et al., 2003, Proc. SPIE-Int. Soc. Opt. Eng. 5221:82-91; Yonzone et al., 2004, Anal. Chem. 76:78-85) silver film over nanosphere (AgFON) substrates or similar substrates. However, the present invention is not limited to *Bacillus* species, as any bacterium that is capable of forming spores which contain CaDPA in the spore case are equally amenable to the present invention. Indeed, those skilled in the art will recognize that a number of pathogenic bacteria form spores. For example, additional spore forming pathogens include, but are not limited to, *B. cereus* (food poisoning) *Clostridium perfringens* (gangrene), and *C. botulinum* (food poisoning). Any of the pathogenic bacteria listed herein could be potentially utilized as a biological weapon. It is contemplated that CaDPA in the spore case of the aforementioned pathogens can be detected using the device and methods of the present invention. Additional examples of spore forming microorganisms can be found in *Bacterial Spore Formers: Probiotics & Emerging Applications*, E. Ricca et al., Eds, Horizon Scientific Press, p. 244, incorporated herein in its entirety.

When the localized surface plasmon resonance (LSPR) maximum of a AgFON substrate closely matches the laser excitation wavelength, the maximum SERS signal intensity results (McFarland, A. D. Ph.D. Thesis, Northwestern University, 2004). In some embodiments, AgFON surfaces are fabricated using 600 nm spheres in order to optimize SERS intensity for 750 nm laser excitation. In some embodiments, the present invention provides detection of a LOD of ~$2.6 \times 10^3$ spores with a data acquisition period of 1 min and a laser power of 50 mW. In other embodiments, the present invention detects LOD of less than $2.6 \times 10^3$ spores. In still further embodiments, the present invention detects a LOD of greater than $2.6 \times 10^3$ spores. Previously published SERS studies of anthrax detection via the CaDPA biomarker were 200 times less sensitive and required 3 times more laser power (Farquharson et al., 2004, Appl. Spectrosc. 58:351-354) than that of the present invention. Similarly, previous published NRS studies were 200,000 times less sensitive and required 8 times more laser power than the compositions and methods of the present invention. The present invention also provides AgFON substrates that provide stable SERS spectra for at least 40 days. The present invention further provides a portable SERS device that produces a SERS spectrum from $10^4$ spores in 5 s using a 1-month-old prefabricated AgFON. Thus, the present invention provides the first compact vibrational spectrometer for the detection of *bacillus* spores.

The present invention contemplates the use of SERS for rapid detection of the anthrax biomarker, CaDPA, using a low-cost, battery-powered, and portable Raman spectrometer, although other biomarkers may be detected. It is further contemplated that the present invention will detect any microorganism that contains CaDPA in detectable quantities. Typically, such spectrometers use an NIR diode laser as the excitation source. One popular diode laser excitation wavelength is 785 nm. To mimic a 785 nm diode laser, the present invention, in some embodiments, uses a CW Ti:Sa laser tuned to 750 nm as the laser excitation source. In some embodiments, the NIR excitation reduces the native fluorescence background from microorganisms. Previously, an important correlation between nanoparticle structure, as reported by the spectral position of the LSPR relative to the laser excitation wavelength, and the SERS intensity was demonstrated. The maximum SERS intensity is obtained from a AgFON surface when the laser excitation wavelength coincides with the LSPR maximum. Since AgFONs are not optically transparent, the reflectivity minimum was used to locate the LSPR maximum. In some embodiments, AgFON substrates for SERS measurements using 750 nm laser excitation are optimized by first measuring the dependence of the LSPR spectral position on nanosphere diameter. FIG. 1 shows the UV-vis diffuse reflectance spectra of AgFON substrates with nanospheres having diameters of 390, 510, and 600 nm. In some embodiments, a AgFON sample was also fabricated using 720 nm diameter spheres. In FIG. 1, the reflectance spectrum of AgFON substrate C (nanosphere diameter, D=600 nm, and mass thickness of Ag film, dm=200 nm) shows a reflectivity minimum near 753 nm, attributable to the excitation of the LSPR of the silver film. This substrate is expected to show the largest intensity for 750 nm laser excitation. To further confirm this expectation, SERS spectra of 1 mM benzenethiol in 20 μL of ethanol on the AgFON substrates with D=390, 510, 600, and 720 nm (FIG. 2) were measured. The largest SERS enhancement of benzenethiol was, in fact, observed from the AgFON with D=600 nm and dm=200 nm (FIG. 2C). In some embodiments, this AgFON substrate was chosen as optimal for the *bacillus* spore detection experiments.

Figure 4:
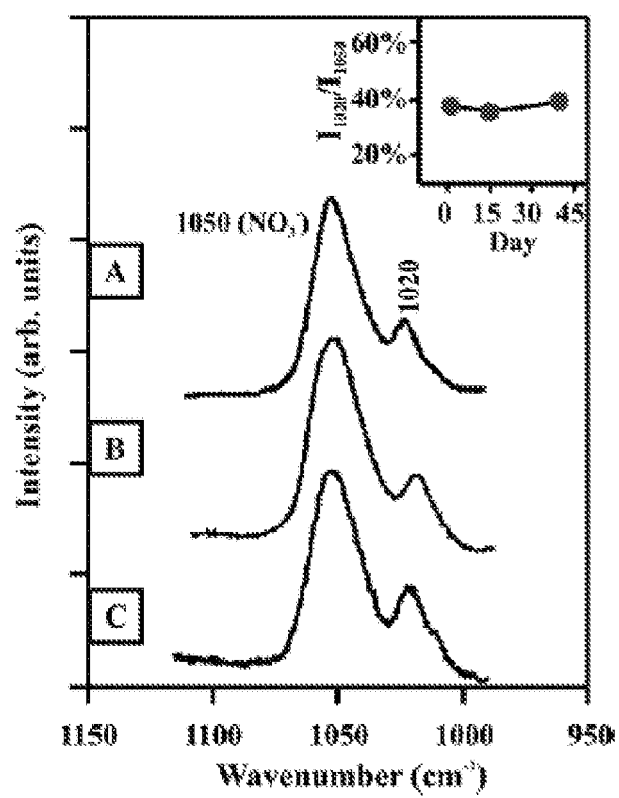
FIG. 4. SERS spectra demonstrate the long-term stability of AgFON substrates, monitored for 1-40 days. SERS spectra of $4.7 \times 10^{-14}$ M spore suspension ($5.6 \times 10^3$ spores in 0.2 µL, 0.02 M $HNO_3$) on AgFON substrates. (A) A 1 day old AgFON, (B) a 15 day old AgFON, and (C) a 40 day old AgFON. The inset shows the intensity ratio (I1020/I1050) variation with time; $\lambda$ex=750 nm, Pex=50 mW, acquisition time=1 min, D=510 nm, and dm=200 nm.
Figure 5:
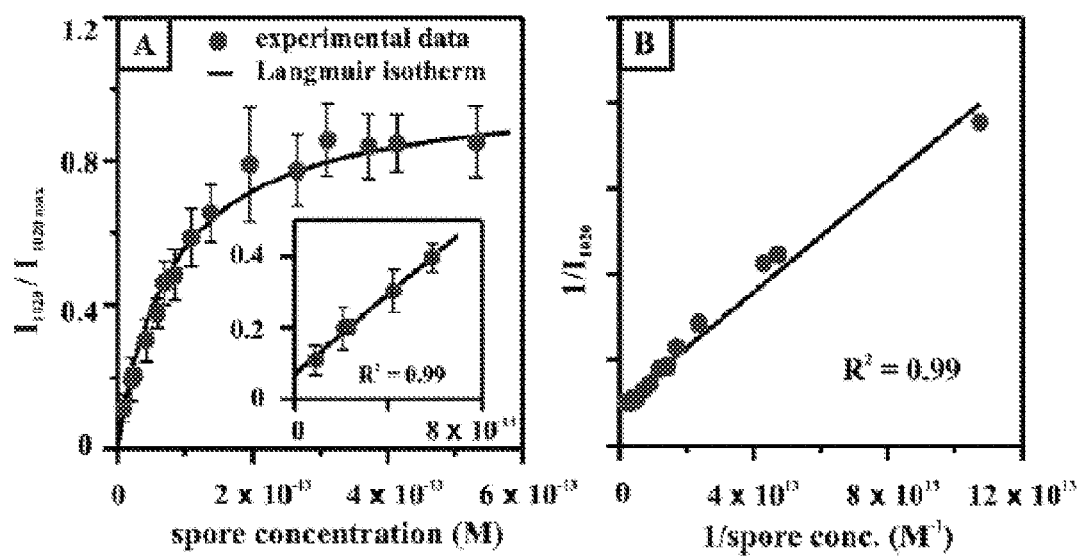
FIG. 5. (A) Adsorption isotherm for *B. subtilis* spore suspension onto an AgFON substrate. I1020 was taken from SERS spectra that correspond to varying spore concentrations in 0.2 µL of 0.02 M $HNO_3$ on AgFON substrates; $\lambda$ex=750 nm, Pex=50 mW, acquisition time=1 min, D=600 nm, and dm=200 nm. A Langmuir curve was generated using eq 1 with Kspore=1.3_1013 M-1. The inset shows the linear range that is used to determine the LOD. Each data point represents the average value from three SERS spectra. Error bars show the standard deviations. (B) Adsorption data fit with the linear form of the Langmuir model (eq 2). The slope and intercept values are used to calculate the adsorption constant.

It is contemplated that an ideal detection system would run unattended for long periods of time, require infrequent maintenance, and operate at low cost. Previous work has demonstrated that bare AgFON surfaces display extremely stable SERS activity when challenged by negative potentials in electrochemical experiments and high temperatures in ultrahigh vacuum experiments (Litorja et al., 2001, J. Phys. Chem. B 105:6907-6915). The present invention provides information regarding the temporal stability of AgFON substrates studied over a period of 40 days. SERS spectra of $4.7 \times 10^{-14}$ M spores ($5.6 \times 10^3$ spores in 0.2 μL, 0.02 M HNO3), well below the anthrax infectious dose of $10^4$ spores, were captured on AgFON substrates of different ages (FIG. 4). The intensity ratios between the strongest CaDPA peak at 1020 cm-1 and the NO3-peak at 1050 cm-1 (I1020/I1050) were measured to quantitatively compare the AgFON substrates of different ages (shown in FIG. 4 inset). Both the CaDPA spectral band positions and intensity patterns remained constant over the course of 40 days, indicating the long-term stability of the AgFON as SERS substrates for potential field-sensing applications. The quantitative relationship between SERS signal intensity and spore concentration is demonstrated in FIG. 5A. Each data point represents the average intensity at 1020 cm-1 from three samples, with the standard deviation shown by the error bars. At low spore concentrations, the peak intensity increases linearly with concentration (FIG. 5A inset). At higher spore concentrations, the response saturates as the adsorption sites on the AgFON substrate become fully occupied. Saturation occurs when the spore concentrations exceed ~$2.0 \times 10^{-13}$ M ($2.4 \times 10^4$ spores in 0.2 μL, 0.02 M $HNO_3$).

Figure 6:
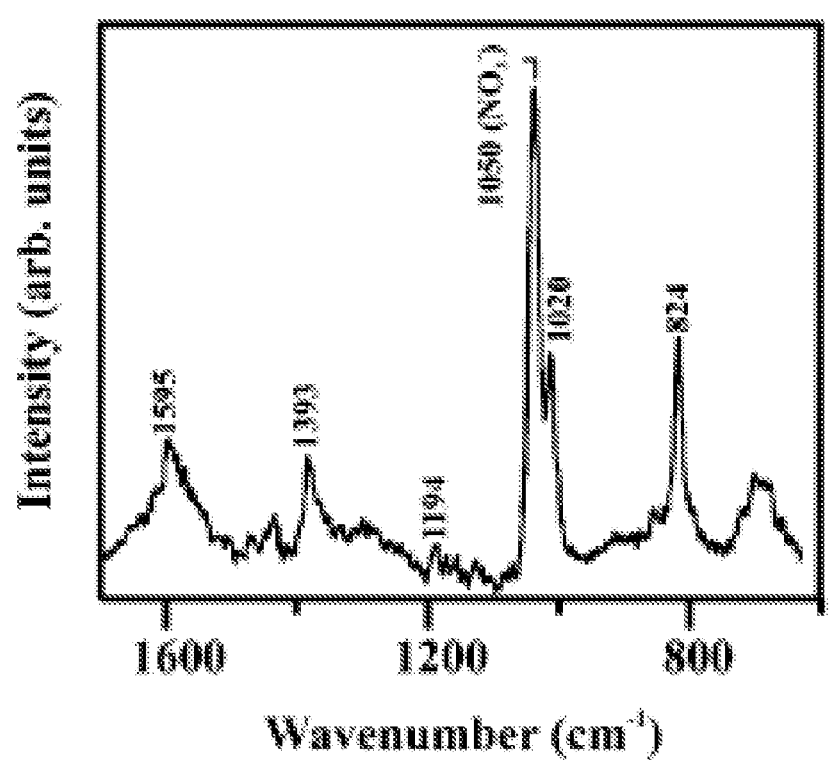
FIG. 6. SERS spectrum of $2.1 \times 10^{-14}$ M spore suspension ($2.6 \times 10^3$ spores in 0.2 µL, 0.02 M $HNO_3$) on AgFON; $\lambda$ex=750 nm, Pex=50 mW, acquisition time=1 min, D=600 nm, and dm=200 nm.

It is preferential that a SERS-based detection system be capable of detecting less than the life-threatening dose of a pathogen in real or near real time. In the present invention, the LOD is the concentration of spores for which the strongest SERS signal of CaDPA at 1020 cm-1 is equal to 3 times the background SERS signal within a 1 min acquisition period. The background signal refers to the SERS intensity from a sample with a spore concentration equal to 0, which is calculated to be the intercept of the low concentration end of the spore adsorption isotherm (FIG. 5A). In some embodiments, lower detection limits are achieved using longer acquisition times. In some embodiments, these aforementioned parameters are used for high throughput, real-time, and on-site analysis of potentially harmful species. For example, the LOD for *B. subtilis* spores, evaluated by extrapolation of the linear concentration range of the adsorption isotherms (FIG. 5A inset), is found to be $2.1 \times 10^{-14}$ M ($2.6 \times 10^3$ spores in 0.2 µL, 0.02 M $HNO_3$). Furthermore, when a similar spore concentration ($2.1 \times 10^{-14}$ M, $2.6 \times 10^3$ spores in 0.2 µL, 0.02 M $HNO_3$) is deposited onto a AgFON surface, a 1 min acquisition yields a SERS spectrum that clearly displays the spore Raman features at 1595, 1393, 1020, and 824 cm-1 (FIG. 6). These data demonstrate that the SERS LOD is below the anthrax infectious dose of $10^4$ spores.

Figure 7:
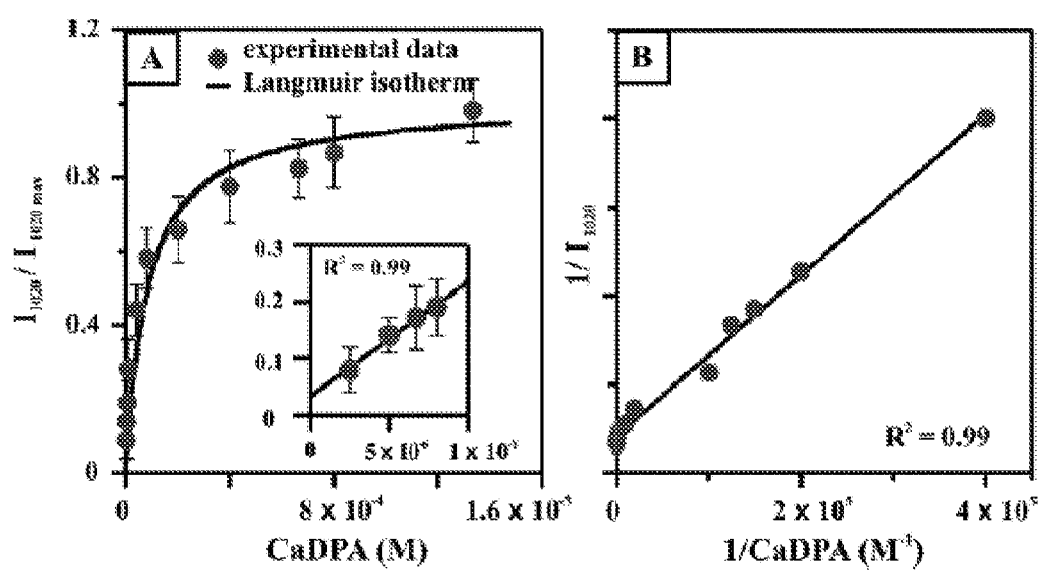
FIG. 7. (A) Adsorption isotherm for CaDPA suspension onto an AgFON substrate. I1020 was taken from SERS spectra that correspond to varying CaDPA concentrations in 0.2 µL of 0.02 M $HNO_3$ on AgFON substrates; $\lambda$ex=750 nm, Pex=50 mW, acquisition time=1 min, D=600 nm, and dm=200 nm. A Langmuir curve was generated using eq 1 with KCaDPA $9.5 \times 10^3$ M-1. The inset shows the linear range that is used to determine the LOD. Each data point represents the average value from three SERS spectra. Error bars show the standard deviations. (B) Adsorption data of CaDPA fit with the linear form of the Langmuir model (eq 2). The slope and intercept values are used to calculate the adsorption constant.

To determine the adsorption capacity of extracted CaDPA on a AgFON, the Langmuir adsorption isotherm was used to fit the data (Jung and Campbell, 2000, J. Phys. Chem. B 104:11168-11178; Jung and Campbell, 2000, Phys. ReV. Lett. 84:5164-5167):

$$\theta = \frac{I_{1020}}{I_{1020,max}} = \frac{K_{spore} \times [\text{spore}]}{1 + K_{spore} \times [\text{spore}]} \quad (2)$$

$$\frac{1}{I_{1020}} = \frac{1}{K_{spore} \times I_{1020,max}} \times \frac{1}{[\text{spore}]} + \frac{1}{I_{1020,max}} \quad (3)$$

where $\theta$ is the coverage of CaDPA on the AgFON; I1020, max is the maximum SERS signal intensity at 1020 cm-1 when all the SERS active sites on AgFON are occupied by CaDPA; [spore] is the concentration of spores (M), and Kspore is the adsorption constant of CaDPA extracted from spores on AgFON (M-1). From eq 3, Kspore is calculated from the ratio between the intercept and the slope. Slope and intercept analyses of the linear fit (FIG. 5B) lead to the value of the adsorption constant, Kspore) $1.7 \times 10^{13}$ M-1. Parallel studies of SERS intensities versus CaDPA concentrations indicate that the LOD is $3.1 \times 10^{-6}$ M in 0.2 µL, 0.02 M $HNO_3$ (FIG. 7A inset), and the adsorption constant for CaDPA, KCaDPA, is $9.0 \times 10^3$ M-1. The ratio between Kspore and KCaDPA represents the extracted amount of CaDPA. Accordingly, it can be estimated that approximately $1.9 \times 10^9$ mol DPA is extracted from 1 mol spores, which corresponds to 3.0% of spore weight. Previous research found that *B. subtilis* spores contain approximately 8.9% DPA by weight. Therefore, the DPA extraction efficiency of 10 min sonication in 0.02 M $HNO_3$ is approximately 34%.

Figure 8:
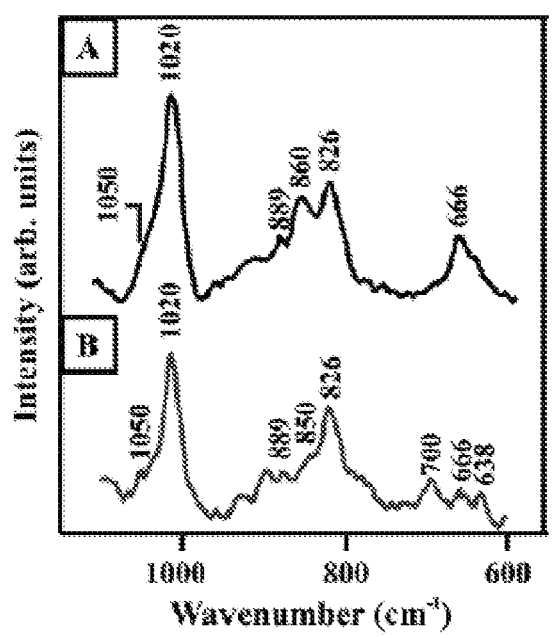
FIG. 8. SERS spectra obtained by the portable Raman spectrometer. (A) SERS spectrum of $8.3 \times 10^{-14}$ M spore suspension ($1.0 \times 10^4$ spores in 0.2 µL, 0.02 M $HNO_3$) on 30 day old AgFON. (B) SERS spectrum of $10^{-4}$ M CaDPA in 0.2 µL of 0.02 M $HNO_3$ on 30 day old AgFON substrate; $\lambda$ex=785 nm, Pex=35 mW, acquisition time=5 s, resolution=15 cm-1, D=600 nm, and dm=200 nm.
Figure 9:
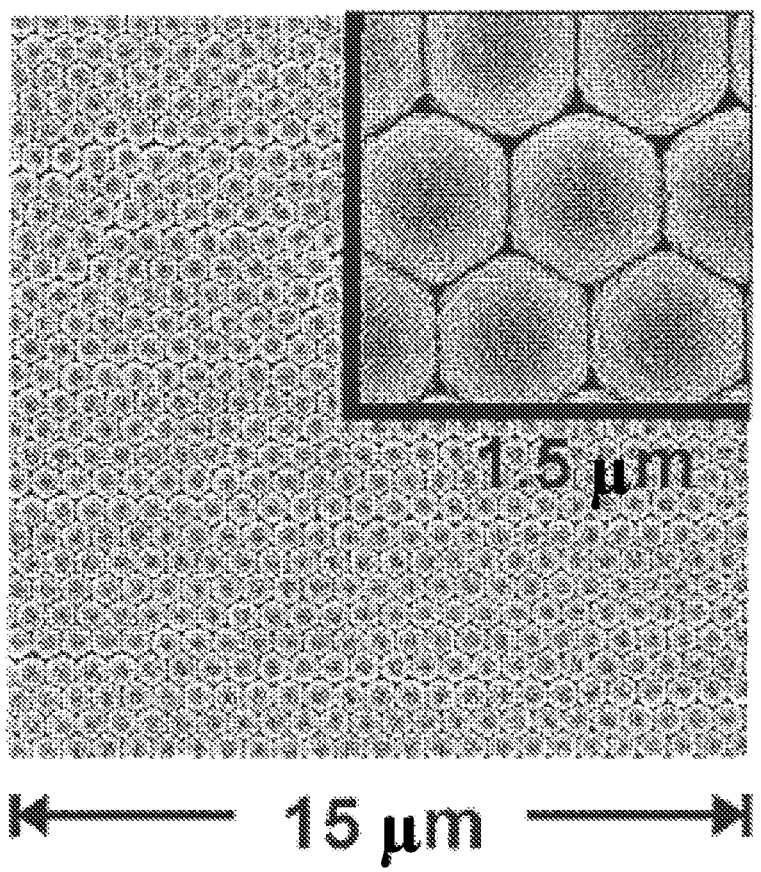
FIG. 9. Exemplary scanning electron microscope images of alumina modified AgFON substrates (D=600 nm, $d_m$=200 nm, and 2 ALD cycles of alumina).
Figure 10:
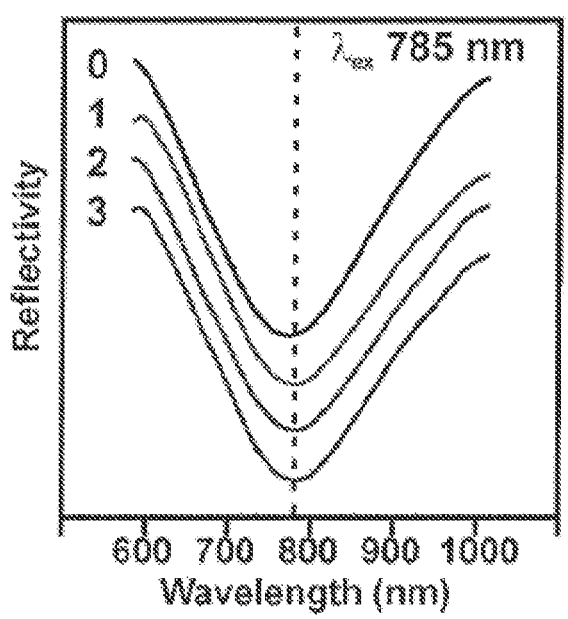
FIG. 10. LSPR reflectance spectra of bare AgFON and alumina modified AgFON substrates with different alumina thickness The ALD cycles of alumina varied from 1 to 3. D=600 nm, $d_m$=200 nm. The vertical dotted line denotes the laser excitation used in the SERS measurements. All reflectance spectra were collected against a mirror-like Ag film over glass surface as a reference in air.

The present invention provides a SERS as a field-portable screening tool by using a compact Raman spectrometer. It is contemplated that the field portable tool be a hand held device, or a portable device capable of being utilized in any location (e.g., outside in the environmental, inside in a building, etc.). Many field-sensing applications require the portability and flexibility not available from conventional laboratory scale spectroscopic equipment. As a first step in this direction, the Raman spectrum from $10^4$ *B. subtilis* spores dosed onto a 1 month old AgFON substrate was readily acquired using a commercially available portable Raman instrument. A high S/N spectrum was achieved within 5 seconds (FIG. 8A). The SERS peak positions and intensity pattern for the spore sample were similar to those of CaDPA recorded utilizing the same device (FIG. 8B). Thus, the present invention provides the first example of using a compact, portable Raman spectrometer for the detection of *bacillus* spores. The portability and ease of use of this type of device with the molecular specificity and spectral sensitivity inherent to SERS open a range of possibilities for detecting bioagents and other chemical threats in an outdoor, field environment as well as in buildings and small, internal and external spaces.

Accordingly, the present invention provides real-time detection of anthrax spores using SERS. In some embodiments, AgFON surfaces (D=600 nm and dm=200 nm) were determined to be SERS intensity-optimized substrates for 750 nm laser excitation. CaDPA was rapidly extracted from *B. subtilis* spores using a 10 min sonication in 0.02 M $HNO_3$, with an extraction efficiency of approximately 34%. In some embodiments, the peaks associated with CaDPA dominate the SERS spectrum of spores. In some embodiments, the strongest peak of CaDPA at 1020 $cm^{-1}$ is used to measure SERS intensity versus spore concentration profiles that yield an adsorption constant, Kspore=$1.7 \times 10^{13}$ M-1. On the basis of the linear portion of the response curve, the LOD of *B. subtilis* spores was estimated to be $2.1 \times 10^{-14}$ M ($2.6 \times 10^3$ spores in 0.2 µL, 0.02 M $HNO_3$) for a 1 min data acquisition period. Furthermore, in some embodiments, the detection level is well below the anthrax infectious dose of $10^4$ spores, and can easily be measured within this acquisition times noted above.

In some embodiments, the present invention provides for alumina coated SERS substrates for detection of microorganisms, such as anthrax. In some embodiments, an ultrathin alumina layer is coated onto silver film over AgFON substrate using atomic layer deposition (ALD). ALD utilized self-limiting surface reactions to control interfacial thickness and compositions with molecular precision. Previous quartz crystal microbalance measurements demonstrated highly uniform layer-by-layer growth of the ALD alumina on Ag nanoparticles with a growth rate of approximately 2 Å per deposition (Whitney et al., 2005, J Phys Chem B 109:20522). The sub-one nanometer thickness is advantageous in preserving sensitivity, because the SERS intensity decays by approximately one order of magnitude for each 2.8 nm separation between the surface and the scatterer (Dieringer et al., 2006, Faraday Discuss 132:9). Details of the intensity decay function are determined by the nanostructure of the underlying silver surface.

The use of ALD alumina in embodiments of the present invention presents several advantages. For example, compared to conventional overlay materials the ultrathin alumina layer is extremely stable to oxidation and high temperature (King, In: *Aluminum and its alloys*, West, E G, Ed Ellis Horwood: New York, 1987; p 313). This maintains the high stability of SERS activity with minimal decrease in signal. Also, alumina is commonly used as a polar adsorbent in chromatographic separations. The relative affinity between Raman scatterers and alumina-modified AgFON substrates is predicted based on their polar interaction, which is well established in the chromatography literature. Generally, molecules with strong polarity, such as carboxylic acids, have high affinity to alumina. Therefore, this novel SERS substrate is an ideal candidate for the detection of carboxylic acids due to the strong polar interaction. Moreover, the scope of analytical applications of SERS is broadened by modifying noble metal surfaces with an analyte-specific affinity coating (Yonzon et al., 2004, Anal Chem 76:78; Driskell et al., 2005, Anal Chem 77:6147; Carron et al., 1992, Environ Sci Technol 26:1950). The coatings used range from, for example, simple alkanes to complex macrocycles with the common theme of containing a thiol group to anchor the coating to a noble metal substrate.

Figure 11:
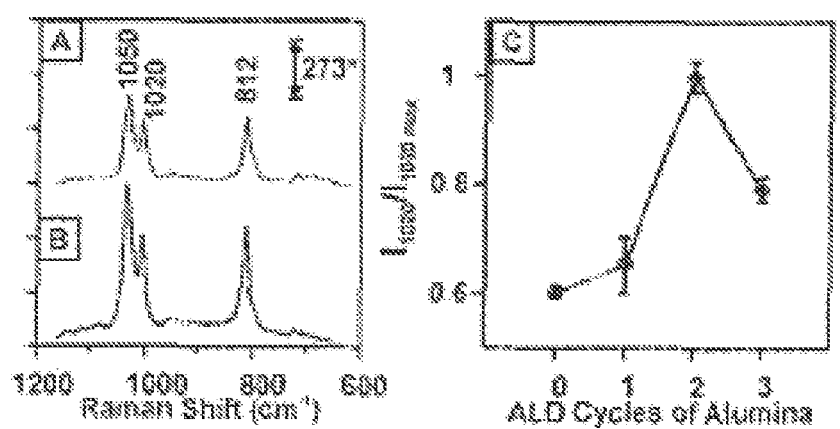
FIG. 11. (A) SERS spectrum of $2 \times 10^5$ M CaDPA in 0.2 µL, 0.02 M $HNO_3$ on alumina modified AgFON substrate (2 ALD cycles of alumina), B) SERS spectrum of CaDPA on bare AgFON substrate, (C) The alumina thickness effect on the SERS intensity. The spectral intensities at 1020 cm$^{-1}$, $I_{1020}$, were plotted versus ALD cycles. $I_{1020}$ was taken from SERS spectra that correspond to varying alumina thickness on the AgFON substrates. Each data point represents the average value from three SERS samples. Error bars show the standard deviations. Laser excitation=785 nm, laser power=50 mW, acquisition time=10 s, D=600 nm, and $d_m$=200 nm. * denotes adu/(s·mW).

In comparison to previously used thiolate SAMs, ALD alumina provides, for example, greater molecular thickness control, greater physical and chemical stability, more complete surface coverage, less signal attenuation due to distance effects, and predictable affinity. In developing embodiments of the present invention, an exemplary optically optimized AgFON substrate was applied to quantitatively detect a biomarker for anthrax, calcium dipicolinate (CaDPA), from *bacillus* spores. In some embodiments, a limit of detection (LOD) of approximately 2,550 anthrax spores was achieved on the AgFON sensor with a data acquisition period of 1 min and a laser power of 50 mW. In further embodiments, affinity between CaDPA and the sensor surface using ALD alumina has been increased, thus increasing the SERS signal intensities. In some embodiments, the alumina-modified sensor demonstrates two-fold improvement in LOD using six times shorter data acquisition time. In some embodiments, the SERS intensity is stable on alumina coated AgFONs for at least 9 months.

FIG. 9 shows an exemplary SEM image of an alumina-modified AgFON substrate with a nanosphere diameter (D) of 590 nm, Ag mass thickness (dm) of 200 nm and 2 ALD cycles of alumina. The low magnification SEM image displays a region of hexagonally packed polystyrene spheres. The inset in FIG. 9, a high magnification image, shows that the top of each nanosphere is not smooth but rather exhibits substructure roughness features 30-50 nm in size. Previously, a detailed wavelength-scanned SERS study of benzenethiol adsorbed on Ag nanoparticle arrays revealed that the maximum SERS enhancement factor occurs for excitation wavelengths ($\lambda_{ex}$) slightly to the blue of the LSPR maximum wavelength for adsorbate-covered nanoparticle arrays (McFarland et al., 2005, J Phys Chem B 109:11279). Additionally, similar observations have been reported based on plasmon-sampled surface-enhanced Raman excitation spectroscopy (Zhang et al., 2005, Am Chem Soc 127:4484; Haynes et al., 2003, Phys Chem B 107:7426).

The plasmon position of FONs is tuned by controlling the size of the spheres used in the underlying nanosphere mask Generally, an increase in polystyrene sphere diameters results in a red shift in LSPR. Here, polystyrene spheres with a diameter of 590 nm were selected to fabricate SERS substrates with the LSPR in the near infrared (NIR) range. In some embodiments, the resulting substrates are optimized for the SERS measurements using NIR laser excitation NIR laser excitation reduces not only the interference from biological fluorescent background, but also the potential for tissue damage due to the low water and tissue absorption of NIR light.

Since AgFONs are not optically transparent, the reflectivity minimum ($\lambda_{min}$) was used to locate the LSPR positions. FIG. 10 shows an exemplary LSPR reflectance spectra of AgFON coated with 0-3 ALD cycles. For reference, the vertical dotted line in FIG. 10 denotes the 785 nm laser excitation used in the SERS measurements. The LSPR $\lambda_{min}$ positions of AgFON coated with 0-3 ALD cycles remain close to the SERS excitation wavelength, ranging between 774 and 781 nm, and are not greatly affected by coating alumina.

In the analysis of biologically, industrially, and environmentally relevant samples, multiple analytes with similar molecular structures are often in competition for the SERS surface. In that situation, the detection selectivity is improved when the affinity between the target analyte and the sensing platform is optimized. In developing embodiments of the present invention, the ability to predict the relative affinity of different molecules on an alumina-modified AgFON substrate was undertaken. Competitive adsorption of dipicolinic acid (a), diacetylpyridine (b), and dimethoxypyridine (c) onto an alumina-modified AgFON surface at room temperature were examined. These pyridine derivative analytes serve as a model system as they provide the unambiguous SERS spectral signatures important to differentiate between the relative adsorption affinities observed during competitive adsorption experiments. On the basis of a thin-layer chromatography (TLC) experiment, the relative affinity between each analyte and alumina was determined to be a>b>c. Therefore, it is contemplated that the SERS spectra of mixed analytes on the alumina-modified AgFON substrates would be dominated by the strongest adsorbate (a). A series of SERS measurements were made by incubating the alumina-modified AgFON substrates in 2 mM analyte in ethanol solutions for 5-6 h. Adsorption of each individual analyte produced a specific SERS signature. It is worth noting that high signal-to-noise SERS spectra were obtained on alumina-modified AgFON substrates even though the adsorbates were not in direct contact with the silver surface. The spectra can be compared with those from equimolar mixtures of pairs of a+b, a+c and b+c. For example, for mixtures that contained a, the spectra was dominated by peaks characteristic of (a) at 1458, 1390, 1042, and 1018 $cm^{-1}$. Similarly, the spectrum for b+c combinations was dominated by signatures of (b).

The high affinity of dipicolinic acid has numerous practical implications. For example, alumina-modified AgFON surfaces are ideal sensing platforms for calcium dipicolinate, a biomarker for *bacillus* spores as previously described. CaDPA was efficiently extracted from spores by sonication in 0.02 M $HNO_3$ and deposited onto ALD alumina-modified AgFON sensors. In some embodiments, the present invention provides for the detection of microorganisms, for example anthrax, on ALD alumina-modified AgFON sensors. As an example of the use of ALD alumina-modified AgFON sensors for microorganism detection, CaDPA was selected as an exemplary probe molecule to test the effect of alumina thickness on SERS detection for *bacillus* spores. FIG. 11A demonstrates an exemplary SERS spectrum of $2\times10^{-5}$ M CaDPA on an AgFON substrate (D=590 nm, dm=200 nm). The SERS bands at 1020 and 812 $cm^{-1}$ are associated with CaDPA, in agreement with previous Raman studies. The peak at 1050 $cm^{-1}$ is from the symmetrical stretching vibration of $NO_3^-$ from nitric acid, which is used as an internal standard to reduce sample-to-sample deviations. For comparison, a parallel SERS experiment was conducted on an alumina-modified AgFON substrate (D=590 nm, $d_m$=200 nm, 2 ALD cycles). The SERS spectrum obtained on the modified substrate demonstrates the same spectral patterns, but higher intensities. A plot of the normalized SERS intensity at 1020 $cm^{-1}$ as a function of ALD cycles is shown in FIG. 11C. The SERS intensity of CaDPA achieves a maximum when the AgFON substrates are modified with 2 ALD cycles of alumina with intensity decreasing with further addition of alumina. The SERS intensity is essentially dependent on both the electromagnetic field and the number of adsorbed molecule. According to previous SERS distance dependence studies, the electromagnetic field decays rapidly when the distance between the scatterers and the silver nanostructures increases. The present invention is not limited to a particular mechanism. Indeed, an understanding of the mechanism is not necessary to practice the present invention. Nonetheless, it is contemplated that the origin of the increase in overall SERS intensity (FIG. 11C) comes from an increase in the number of scattering molecules. In other words, the adsorption affinity of CaDPA to alumina is anticipated to be greater than that of CaDPA to silver.

The quantitative relationship between SERS signal intensity and CaDPA concentration is such that at low concentrations, the peak intensity increases linearly with concentration. As described herein, LOD is defined as the concentration of CaDPA for which the strongest SERS signal of CaDPA at 1020 cm$^{-1}$ is equal to three times the background SERS signal for a 10-sec acquisition period and 50 mW laser power. The background signal refers to the SERS intensity from a sample with a CaDPA concentration equal to zero, which is calculated to be the intercept of the low concentration end of the adsorption isotherm. Although lower detection limits can be achieved, for example, using longer acquisition times and higher laser power, these parameters are reasonable for high throughput, real-time, and on-site analysis of potentially harmful species. The LOD for CaDPA, evaluated by extrapolation of the linear concentration range of the adsorption isotherms, was found to be $1.9 \times 10^{-6}$ M (in 0.2 µL, 0.02 M HNO$_3$). At higher CaDPA concentrations, the response saturates as the adsorption sites on the alumina modified AgFON substrate become fully occupied. Saturation occurs when CaDPA concentrations exceed approximately $1.5 \times 10^{-4}$ M (in 0.2 µL, 0.02 M HNO$_3$). To determine the adsorption capacity of extracted CaDPA on an alumina modified AgFON, the Langmuir adsorption isotherm was used to fit the data as described in Equations 2 and 3 where [spore] is the concentration of CaDPA (M); and $K_{spore}$ is the adsorption constant of CaDPA to alumina-modified AgFON (M$^{-1}$). From equation 3, $K_{spore}$ is calculated from the ratio between the intercept and the slope. Slope and intercept analyses of the linear fit leads to the value of the adsorption constant $K_{spore} = 4.9 \times 10^4$ M$^{-1}$.

Figure 12:
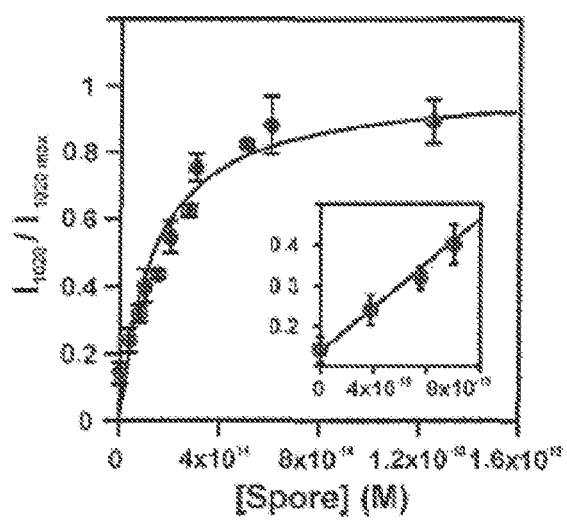
FIG. 12. Adsorption isotherm for *B. subtilis* spore suspension on alumina modified AgFON substrates was taken from SERS spectra that correspond to varying spore concentrations in 0.2 μL, 0.02 M $HNO_3$, on the substrates. The inset shows the linear range that was used to determine the LOD. Each data point represents the average value from three SERS samples. Error bars show the standard deviations. Law excitation=785 nm, laser power=50 mW, acquisition time=10 s, D=600 nm, $d_m$=200 nm, and 2 ALD cycles of alumina.

Previous SERS studies on bare AgFON substrates indicated that the adsorption constant for CaDPA was $9.0 \times 10^3$ M$^{-1}$ and the LOD was $3.1 \times 10^{-6}$ M (laser excitation=750 nm, laser power=50 mW, acquisition time=60 s). The affinity between CaDPA and alumina-modified AgFON is approximately 5 times stronger than that of bare AgFON. As such, the change in surface chemistry by the addition of alumina improves the LOD of CaDPA. The SERS spectra of a *bacillus* spore suspension are dominated by CaDPA on alumina modified AgFON as illustrated in FIG. 12, the parallel studies of SERS intensities at 1020 cm$^{-1}$ versus spore concentrations indicate that the LOD is approximately $1.4 \times 10^3$ spores in 0.2 µL, 0.02 M HNO$_3$, and the adsorption constant for CaDPA extracted from spores, $K_{spore}$ is $9.0 \times 10^{13}$ M$^{-1}$. In contrast, the adsorption constant was $1.7 \times 10^{13}$ M$^{-1}$ for extracted CaDPA on bare AgFON surface and the LOD was $2.6 \times 10^3$ spores (laser excitation=750 nm, laser power=50 mW, acquisition time=60 s).

Figure 13:
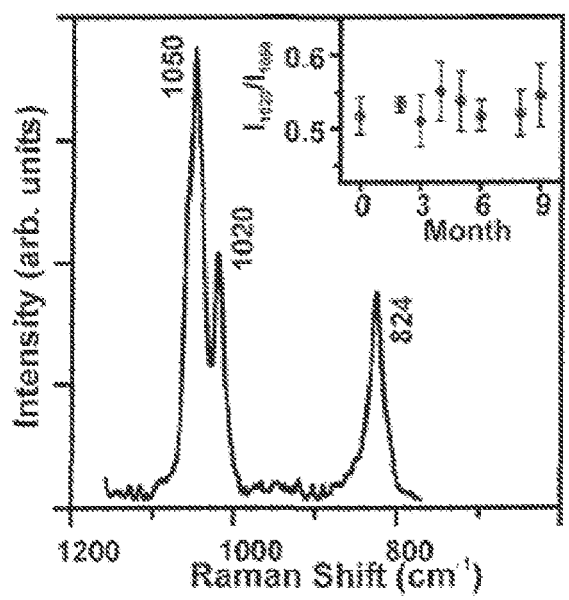
FIG. 13. A SERS spectrum of $3.0\times10^{-14}$ M spores ($3\,6\times10^3$ spores in 0.2 μL, 0.02 M $HNO_3$) on a 9 month old alumina modified AgFON substrate. The inset shows the intensity ratio ($I_{1020}/I_{1050}$) variation with time. Laser excitation=785 nm, laser power=50 mW, acquisition time=10 s D=590 nm, $d_m$=200 nm, and 2 ALD cycles of alumina.

It is contemplated that desirable attributes for a sensor device include, but are not limited to, stability for long periods of time and infrequent maintenance. It is demonstrated herein that temporal stability of alumina modified AgFON substrates (D=590 nm, $d_m$=200 nm, 2 ALD cycles) was studied over a period of 9 months. The alumina-modified AgFON substrates were stored in Petri dishes in the dark prior to use. SERS spectra of $3.0 \times 10^{-14}$ M spores ($3.6 \times 10^3$ spores in 0.2 µL, 0.02 M HNO$_3$) were captured on alumina-modified AgFON substrates of different ages. FIG. 13 shows a representative SERS spectrum on a 9 month old alumina-modified AgFON substrate prior to use. The intensity ratios between the strongest CaDPA peak at 1020 cm$^{-1}$ and the NO$_3^-$ peak at 1050 cm$^{-1}$ ($I_{1020}/I_{1050}$) were measured to quantitatively compare the substrates of different ages (FIG. 13 inset). The temporal stability of alumina-modified AgFON substrates is demonstrated in that the SERS intensities of extracted CaDPA remained constant over the course of 9 months. The excellent long term stability coupled with precision and low cost makes alumina-modified AgFON substrates ideally suited for potential field sensing applications.

EXPERIMENTATION

The following examples serve to illustrate certain preferred embodiments and aspects of the present invention and are not to be construed as limiting the scope thereof.

Chemicals used were of reagent grade or better. Ag (99.99%) was purchased from D. F. Goldsmith (Evanston, Ill.). Glass substrates were 18 mm diameter, No. 2 cover slips from Fisher Scientific (Pittsburgh, Pa.). Pretreatment of substrates required H2SO4, H2O2, and NH4OH, all of which were purchased from Fisher Scientific (Fairlawn, N.J.). Surfactant-free white carboxyl-functionalized polystyrene latex nanospheres with diameters of 390, 510, 600, and 720 nm were obtained from Duke Scientific Corporation (Palo Alto, Calif.) and Interfacial Dynamics Corporation (Portland, Oreg.). Tungsten vapor deposition boats were purchased from R. D. Mathis (Long Beach, Calif.). Nitric acid 70% (Fisher Scientific), dipicolinic acid (2,6-pyridinedicarboxylic acid, DPA), calcium hydroxide, and benzenethiol (Aldrich Chemical Co., Milwaukee, Wis.) were used as purchased. Water (18.2 MΩ/cm) was obtained from an ultrafilter system (Milli-Q, Millipore, Marlborough, Mass.). Calcium dipicolinate (CaDPA) was prepared from DPA and calcium hydroxide according to the method of Beiley and co-workers.

The SERS apparatus comprising a battery-powered Raman spectrometer (model Inspector Raman, diode laser excitation wavelength λex 785 nm) was purchased from DeltaNu (Laramie, Wyo.) and was used to demonstrate the feasibility of a field-portable device for spore detection. The remaining data were acquired using a macro-Raman system. This system comprises an interference filter (Coherent, Santa Clara, Calif.), a 1 in. holographic edge filter (Physical Optics Corporation, Torrance, Calif.), a single-grating monochromator with the entrance slit set at 100 µm (model VM-505, Acton Research Corporation, Acton, Mass.), a liquid-N2-cooled CCD detector (Model Spec-10:400B, Roper Scientific, Trenton, N.J.), and a data acquisition system (Photometrics, Tucson, Ariz.). A titanium-sapphire laser (CW Ti:Sa, Model 3900, Spectra Physics, Mountain View, Calif.) pumped by a solid-state diode laser (Model Millenia Vs, Spectra Physics) was used to generate λex of 750 nm. All of the measurements were performed in ambient conditions.

Thin layer chromatography (TLC) analysis were performed on aluminum backed aluminum oxide 60 F-254 neutral with a 0.1 mm layer thickness (type E, E. Merck, Darmstadt, Germany) in 10:1 v/v hexanes:ethyl acetate.

Example 1

Microbial Culture

*B. subtilis* was purchased from the American Type Culture Collection (Manassas, Va.). Spore cultures were cultivated by spreading the vegetative cells on sterile nutrient agar plates (Fisher Scientific), followed by incubating at 30° C. for 6 days. The cultures were washed from the plates using sterile water and centrifuged at 12 000 g for 10 min. The centrifuging procedure was repeated five times. The lyophilized spores were kept at 2-4° C. prior to use. Approximately 1 g of sample was determined to contain $5.6\times10^{10}$ spores by optical microscopic measurements (data not shown). The spore suspension was made by dissolving spores in 0.02 M $HNO_3$ solution and by sonicating for 10 min.

Example 2

Extraction of CaDPA from Spores

CaDPA was extracted from spores by sonicating in 0.02 M $HNO_3$ solution for 10 min. This concentration of the $HNO_3$ solution was selected because of its capability of extraction and its benign effect on the AgFON SERS activity. To test the efficiency of this extraction method, a $3.1\times10^{-13}$ M spore suspension ($3.7\times10^4$ spores in 0.2 µL, 0.02 M $HNO_3$) was deposited onto an AgFON substrate (D=600 nm, dm=200 nm). The sample was allowed to evaporate for less than 1 min. A high signal to-noise ratio (S/N) SERS spectrum was obtained in 1 min (FIG. 3A). For comparison, a parallel SERS experiment was conducted using $5.0\times10^{-4}$ M CaDPA (FIG. 3B). The SERS spectrum of *B. subtilis* spores is dominated by bands associated with CaDPA, in agreement with the previous Raman studies on *bacillus* spores. The SERS spectra in FIG. 3, however, display noticeable differences at 1595 cm-1, which are from the acid form of dipicolinate (Carmona, 1980, Spectrochim. Acta, Part A 36A:705-712).

The peak at 1050 $cm^{-1}$ in FIG. 3A is from the symmetrical stretching vibration of $NO^{3-}$ (Mosier-Boss and Lieberman, 2000, Appl. Spectrosc. 54:1126-1135). The $NO^{3-}$ peak can be used as an internal standard to reduce the sample-to-sample deviations if desired.

Example 3

AgFON Substrate Fabrication

Glass substrates were pretreated in two steps; 1) Piranha etch, 3:1 $H_2SO_4$/30% $H_2O_2$ at 80° C. for 1 h, was used to clean the substrate, and 2) base treatment, of 5:1:1 $H_2O$/$NH_4OH$/30% $H_2O_2$ with sonication for 1 h was used to render the surface hydrophilic. Approximately 2 µL of the nanosphere suspension (4% solids) was drop coated onto each substrate and allowed to dry in ambient conditions. The metal films were deposited in a modified Consolidated Vacuum Corporation vapor deposition system with a base pressure of $10^{-6}$ Torr (Hulteen and Van Duyne, 1995, J. Vac. Sci. Technol. A 13:1553-1558). The deposition rates for each film (10 Å/s) were measured using a Leybold Inficon XTM/2 quartz crystal microbalance (QCM) (East Syracuse, N.Y.). AgFON substrates were stored in the dark at room temperature prior to use.

Alternatively, 2D self-assembled monolayer masks of nanospheres were fabricated by drop-coating approximately 2.54, of undiluted nanosphere solution (10% solid) on the pretreated substrates. The nanospheres were allowed to dry in ambient conditions and silver was deposited by electron beam (e-beam) deposition in a Kurt J. Lesker Axxis e-beam deposition system (Pittsburgh, Pa.) with a base pressure of $10^{-6}$ Torr. The mass thickness and deposition rate (1 Å/sec) was monitored using a Sigma Instruments 6 MHz gold plated QCM (Fort Collins, Colo.). After the Ag deposition, the nanosphere masks were removed by sonication in absolute ethanol for 3 min. Hemispheroidal Ag nanoparticles were fabricated by annealing Ag triangular nanoparticles at 300° C. for 1 hr at approximately 1 Torr under $N_2$. The Ag nanoparticles were solvent annealed using hexanes and methanol in a home built flow cell to ensure the stabilization of the LSPR extinction spectra (Malinsky et al., 2001, J. Am. Chem. Soc 123:1471-1482). Dry $N_2$ gas and solvent were cycled through the flow cell until the $\lambda_{max}$ of the nanoparticle arrays was stabilized. The samples were rinsed with absolute ethanol and dried under $N_2$.

Example 4

Spectroscopy

UV-Vis Diffuse reflectance spectroscopy measurements were carried out using an Ocean Optics (Dunedin, Fla.) SD2000 spectrometer coupled to a reflection probe (Ocean Optics) and a halogen lamp (Model F-O-Lite H, World Precision Instruments, Sarasota, Fla.). The reflection probe consists of a tight bundle of 13 optical fibers (12 illumination fibers around a collection fiber) with a usable wavelength range of 400-900 nm. All reflectance spectra were collected against a mirror like Ag film over glass substrate as a reference.

Alumina ($Al_2O_3$) film thicknesses were measure by VASE using an M-2000V from J.A. Wollam Co. VASE measurements were taken on alumina ALD films fabricated on a 50 nm Ag film deposited by e-beam. The alumina ALD on the Ag film was done concurrently with alumina ALD on the Ag nanoparticles.

LSPR extinction measurements of the silver nanoparticle arrays were obtained using a M-2000V in transmission mode.

The surface composition of a 50 nm Ag film deposited by e-beam on glass was analyzed by XPS. The measurements were performed using MgKa (1253 6 eV) radiation and a hemispherical electron energy analyzer (HEA). The spectra were recorded in fixed absolute resolution (FAT) mode of the HEA with pass energy of 44 eV (for survey spectra) and 22 eV (for detailed measurements of core level peaks). The electrons were collected from the area with an elliptical shape with dimensions of 4 mm×3 mm. Survey spectra with an energy step of 1 ev and precision measurements of core level photoelectron lines Cls, Si2p, Ols, Cl1s as well as a valence band with the energy step of 0.2 eV were recorded. The spectrometer calibration was performed using the gold XPS emission line ($Au4_{f7/2}$ with a binding energy of 84 eV). The residual vacuum in the analyzing chamber was $4\times10^{-10}$ mbar. Processing of the obtained XPS spectra was performed using the CasaXPS software. Measured peaks were corrected for inelastic scattering by subtracting the Shirley background from the raw spectra, followed by the fitting of peaks by using the asymmetric pseudo-Voigt shape peaks with different relative content of Gaussian and Lorentzian components.

Example 5

Atomic Layer Deposition (ALD)

Alumina films were fabricated on the Ag nanoparticles by ALD. The reactor utilized in these experiments has been previously reported (Whitney et al., 2005). Trimethyl aluminum (TMA) and deionized $H_2O$ vapors were alternately pulsed through the reaction chamber utilizing $N_2$ as the carrier gas at a mass flow rate of 360 sccm and a pressure of 1 Torr using a growth temperature of 50° C. One complete ALD cycle takes approximately 42 s, and includes 4 steps: (1) TMA reactant exposure time=1 s, (2) $N_2$ purge following TMA exposure time=10 s, (3) $H_2O$ reactant exposure time=1 s, and (4) $N_2$ purge following $H_2O$ exposure time=30 s. Long purge times are necessary at low temperatures to prevent chemical vapor deposition of alumina. It was determined that acceptable layer-by-layer growth of the ALD alumina on Ag surfaces resulted from an average rate of approximately 2 Å/cycle. As such, this result greatly simplifies the interpretation of the thickness of the alumina overlayers, which are deduced easily from the number of ALD cycles.

Scanning Electron Microscopy (SEM) images of alumina coated AgFON were observed with a Hitatchi S-4700-11 SEM.

Example 6

Quartz Crystal Microbalance Measurements

Details of in situ QCM measurements have been reported previously (Elam et al., 2002, Rev. Sci Instrum 73:2981-2987). Briefly, the QCM experiments utilized polished sensors (Colorado Crystal Corporation, Part #CCAT1BK-1007-000) installed in a Maxtek BSH-150 bakeable sensor-head. Prior to installation, an Ag film with a thickness of 50 nm was deposited onto the QCM sensor by e-beam. To prevent deposition on the back surface of the sensor during the ALD experiments, the sensor housing was continuously purged with ultrahigh purity $N_2$ and the gap between the front surface of the sensor and the crystal holder was filled using a high temperature conducting epoxy (Epotek PI01 1). To minimize temperature-induced apparent mass changes, a uniform temperature distribution was established near the QCM by adjusting the temperature setpoints and heater power distribution of four separate temperature-controlled heating zones. The QCM signals were monitored using a Maxtek TM400 thickness monitor with a mass resolution of 0.375 ng/cm$^2$ (0.01 Å $Al_2O_3$) at 10 measurements per second.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A sensor comprising:
   i) a substrate,
   ii) nanospheres deposited on the substrate,
   iii) a silver film over the nanospheres, and
   iv) an alumina layer coated over the silver film;
wherein the alumina layer is the top layer of the sensor.

2. The sensor of claim 1, wherein the alumina is layer is of Angstrom thickness.

3. The sensor of claim 1, wherein the silver film underlies the alumina.

4. The sensor of claim 1, wherein said sensor is a surface-enhanced Raman biosensor.

5. The sensor of claim 1, wherein said substrate comprises a glass surface.

6. The sensor of claim 1, wherein said nanosphere has a diameter of 390-720 nm.

7. The sensor of claim 1, wherein said nanosphere has a diameter of 500-700 nm.

8. The sensor of claim 1, wherein said silver film has a mass thickness of 200 nm.

* * * * *

UNITED STATES PATENT AND TRADEMARK OFFICE
CERTIFICATE OF CORRECTION

PATENT NO.         : 8,628,727 B2
APPLICATION NO.    : 11/846352
DATED              : January 14, 2014
INVENTOR(S)        : Richard P. Van Duyne et al.

It is certified that error appears in the above-identified patent and that said Letters Patent is hereby corrected as shown below:

On the title page item (73), should read:
Assignee:   Northwestern University, Evanston, IL (US)
            UChicago Argonne, LLC, Chicago, IL (US)

Signed and Sealed this
Fifteenth Day of December, 2015

Michelle K. Lee
*Director of the United States Patent and Trademark Office*